US006303373B1

(12) United States Patent
Bogan et al.

(10) Patent No.: US 6,303,373 B1
(45) Date of Patent: Oct. 16, 2001

(54) METHOD OF MEASURING PLASMA MEMBRANE TARGETING OF GLUT4

(75) Inventors: Jonathan S. Bogan, Belmont; Harvey F. Lodish, Brookline, both of MA (US)

(73) Assignees: Whitehead Institute for Biomedical Research, Cambridge; The General Hospital Corporation, Boston, both of MA (US)

( * ) Notice: Subject to any disclaimer, the term of this patent is extended or adjusted under 35 U.S.C. 154(b) by 0 days.

(21) Appl. No.: 09/591,025

(22) Filed: Jun. 9, 2000

Related U.S. Application Data

(60) Provisional application No. 60/154,078, filed on Sep. 15, 1999, and provisional application No. 60/138,237, filed on Jun. 9, 1999.

(51) Int. Cl.[7] ..................... C12N 5/00; C12N 15/00; C07H 21/02; C07K 14/00

(52) U.S. Cl. ..................... 435/325; 435/320.1; 435/6; 435/69.1; 536/23.1; 530/350

(58) Field of Search ..................... 435/3, 6, 69.1, 435/70.3, 325, 252.3; 514/2; 530/350

(56) References Cited

PUBLICATIONS

Aledo, J.C., et al., "Identification and characterization of two distinct intracellular GLUT4 pools in rat skeletal muscle: evidence for an endosomal and an insulin–sensitive GLUT4 compartment", *Biochem J.,* 325:727–732 (1997).

Araki,S., et al., "Subcellular trafficking kinetics of GLUT4 mutated at the N– and C– termini", *Biochem J.,* 315:153–159 (1996).

Asano, T.A., et al., "Domains Responsible for the Differential Targeting of Glucose Transporter Isoforms", *J. Biol. Chem.,* 267(27):19636–19641 (1992).

Baldini, G., et al., "Cloning of a Rab3 isotype predominately expressed in adipocytes", *Proc. Natl. Acad. Sci. USA,* 89:5049–5052 (1992).

Bogan, J.S. and Lodish, H.F., "Two Compartments for Insulin–stimulated Exocytosis in 3T3–L1 Adipocytes Defined by Endogenous ACRP30 and GLUT4", *J. Cell Biol.,* 146(3):609–620 (1999).

Brown, D., et al., "Cellular mechanisms of aquaporin trafficking", *Am. J. Physiol.,* 275(3):F328–331 (1998).

Caplan, M.J., "Gastric $H^+/K^+$–ATPase:targeting signals in the regulation of physiologic function", *Curr Opin. Cell Biol.,* 10(4):468–473 (1998).

Charron, M.J., et al., "GLUT4 Gene Regulation and Manipulation", *J. Biol. Chem.,* 274(6):3253–3256 (1999).

Charron, M.J., et al. "A glucose transport protein expressed predominately in insulin–responsive tissues", Proc. Natl. Acad. Sci. USA, 86(8):2535–2539 (1989).

Clark, A.E., et al, "Determination of the rates of appearance and loss of glucose transporters at the cell surface of rat adipose cells", *Biochem. J.,* 278:235–241 (1991).

(List continued on next page.)

*Primary Examiner*—Karen Cochrane Carlson
*Assistant Examiner*—Chih-Min Kam
(74) *Attorney, Agent, or Firm*—Hamilton, Brook, Smith & Reynolds, P.C.

(57) ABSTRACT

A method of measuring translocation of a protein in cells from an intracellular location to a plasma membrane or from the plasma membrane to an intracellular location, with particular reference to GLUT4 and modified GLUT4 useful in the method.

28 Claims, 12 Drawing Sheets

(5 of 12 Drawing Sheet(s) Filed in Color)

Basal

GFP

Epitope tag is sequestered within the cell

Insulin-stimulated

Epitope tag is externalized

OTHER PUBLICATIONS

Cushman, S.W. and Wardzala, L.J., "Potential Mechanism of Insulin Action on Glucose Transport in the Isolated Rat Adipose Cell", *J. Biol. Chem.,* 255(10):4758–4762 (1980).

Czech, M.P., et al., "Exofacial Epitope–tagged Glucose Transporter Chimeras Reveal COOH–Terminal Sequences Governing Cellular Localization", *J. Cell Biol.,* 123(1):127–135 (1993).

Dobson, S.P., et al., "Dynamics of insulin–stimulated translocation of GLUT4 in single living cells visualised using green fluorescent protein", *FEBS Lett,.* 393:179–184 (1996).

El–Jack, A.K., et al., "The Formation of an Insulin–responsive Vesicular Cargo Compartment Is an Early Event in 3T3–L1 Adipocyte Differentiation", *Mol. Biol. Cell.,* 10(5):1581–1592 (1999).

Frost, S.C. and Lane, M.D., "Evidence for the Involvement of Vicinal Sulfhydryl Groups in Insulin–activated Hexose Transport by 3T3–L1 Adipocytes", *J. Biol. Chem.,* 260(5):2646–2652 (1985).

Green, H. and Kehinde, O., "An Established Preadipose Cell Line and its Differentiation in Culture II. Factors Affecting the Adipose Conversion", *Cell,* 5:19–27 (1975).

Gustafson, C.E., et al., Data Submission, "Vasopressin regulated trafficking of a green fluorescent protein–aquaporin 2 chimera in LLC–PK1 cells", Accession No. PREV199800473658, (1998). abstract.

Haney, P.M., et al., "Intracellular Targeting of the Insulin––regulatable Glucose Transporter (GLUT4) Is Isoform Specific and Independent of Cell Type", *J. Cell Biol.,* 114(4):689–699 (1991).

Herman, G.A., et al., "A distinct class of intracellular storage vesicles, identified by expression of the glucose transporter GLUT4", *Proc. Natl. Acad. Sci. USA,* 91:12750–12754 (1994).

Holman, G.D., et al., "Insulin–stimulated GLUT4 Glucose Transporter Recycling", *J. Biol. Chem.,* 269(26):17516–17524 (1994).

Holman, G.D. and Cushman, S.W., "Subcellular trafficking of GLUT4 in insulin target cells", *Semin Cell Dev. Biol.,* 7(2):259–268 (1996).

Holman, G.D., et al., "Cell Surface Labeling of Glucose Transporter Isoform GLUT4 by Bis–mannose Photolabel", *J. Biol. Chem.,* 265(30):18172–18179 (1990).

Hudson, A.W., et al., "Isoform–specific Subcellular Targeting of Glucose Transporters in Mouse Fibroblasts", *J. Cell Biol.,* 116(3):785–797 (1992).

Inoue, T., et al., "SNAP–23 in rat kidney: colocalization with aquaproin–2 in collecting duct vesicles", *Am. J. Physiol.,* 275(5):F752–760 (1998).

Ishii, K., et al., "Possible domains responsible for intracellular targeting and insulin–dependent translocation of glucose transporter type 4", *Biochem J.,* 309:813–823 (1995).

Jhun, B.H., et al., "Effects of insulin on Steady State Kinetics of GLUT4 Subcellular Distribution in Rat Adipocytes", *J. Biol. Chem.,* 267(25):17710–17715 (1992).

Johnson, A.O., et al., "Identification of an Insulin–responsive, Slow Endocytic Recycling Mechanism in Chinese Hamster Ovary Cells", *J. Biol. Chem.,* 273(28):17968–17977 (1998).

Kanai, F., et al., "Direct Demonstration of Insulin–induced GLUT4 Translocation to the Surface of Intact Cells by Insertion of a c–myc Epitope into an Exofacial GLUT4 Domain", *J. Biol. Chem.,* 268(19):14523–14526 (1993).

Kandror, K.V. and Pilch, P.F., "Multiple endosomal recycling pathways in rat adipose cells", *Biochem J.,* 331:829–835 (1998).

Kao, A.W., et al., "Expression of a Dominant Interfering Dynamin Mutant in 3T3L1 Adipocytes Inhibits GLUT4 Endocytosis without Affecting Insulin Signaling", *J. Biol. Chem.,* 273(39):25450–25457 (1998).

Kinsella, T.M. and Nolan, G.P., "Episomal Vectors Rapidly and Stably Produce High–Titer Recombinant Retrovirus", *Hum. Gene. Ther.,* 7(12):1405–1413 (1996).

Knepper, M.A. and Inoue, T., "Regulation of aquaporin–2 water channel trafficking by vasopressin", *Curr. Opin. Cell Biol.,* 9(4):560–564 (1997).

Li, W.M. and McNeill, J.H., "Quantitative Methods for Measuring the Insulin–regulatable Glucose Transporter (GLUT4)", *J. Pharmacol. Toxicol. Methods,* 38(1):1–10 (1997).

Livingston, C., et al., "Compartment ablation analysis of the insulin–responsive glucose transporter (GLUT4) in 3T3–L1 adipocytes", *Biochem J.,* 315:487–495 (1996).

Mandon, B., et al., "Syntaxin–4 Is Localized to the Apical Plasma Membrane of Rat Renal Collecting Duct Cells: Possible Role in Aquarporin–2 Trafficking", *J. Clin. Invest.,* 98(4):906–913 (1996).

Marshall, B.A., et al., "Domains That Confer Intracellular Sequestration of the Glut4 Glucose Transporter in Xenopus Oocytes", *J. Biol. Chem.,* 268(35):26193–26199 (1993).

Martin, S., et al., "The glucose transporter GLUT4 and the aminopeptidase vp165 colocalise in tubulo–vesicular elements in adipocytes and cardiomyocytes", *Journal of Cell Science,* 110(18):2281–2291 (1997).

Melvin, D.R., et al., "Analysis of Amino and Carboxy Terminal GLUT–4 Targeting Motifs in 3T3–L1 Adipocytes Using an Endosomal Ablation Technique", *Biochemistry,* 38(5):1456–1462 (1999).

Moyer, D.B., et al., Membrane Trafficking of the Cystic Fibrosis Gene Product, Cystic Fibrosis Transmembrane Conductance Regulator, Tagged with Green Fluorescent Protein in Madin–Darby Canine Kidney Cells, *J. Bio. Chem.,* 273(34):21759–21768 (1998).

Nielsen, S., et al., "Expression of VAMP2–like Protin in Kidney Collecting Duct Intracellular Vesicles", *J. Clin Invest.,* 96:1834–1844 (1995).

Oatey, P.B., et al., "GLUT4 vesicle dynamics in living 3T3 L1 adipocytes visualized with green–fluorescent protein", *Biochem J.,* 327:637–642 (1997).

Onishi, M., et al., "Applications of retrovirus–mediated expression cloning", *Exp. Hematol.,* 24(2):324–329 (1996).

Pessin, J.E.,et al., "Molecular Basis of Insulin–stimulated GLUT4 Vesicle Trafficking", *J. Biol. Chem.,* 274(5):2593–2596 (1999).

Rea, S. and James, D.E., "Moving GLUT4 The Biogenesis and Trafficking of GLUT4 Storage Vesicles", *Diabetes,* 46:1667–1677 (1997).

Reed B.C., and Lane, M.D., "Insulin receptor synthesis and turnover in differentiating 3T3–L1 preadipocytes", *Proc. Natl. Acad. Sci. USA,* 77(1):285–289 (1980).*

Robinson, L.J., et al., "Translocation of the Glucose Transporter (GLUT4) to the Cell Surface in Permeabilized 3T3–L1 Adipocytes: Effects of ATP, Insulin, and GTPγS and Localization of GLUT4 to Clathrin Lattices", *J. Cell Biol.,* 117(6):1181–1196 (1992).*

Ross, S.A., et al., "Increased intracellular sequestration of the insulin–regulated aminopeptidase upon differentiation of 3T3–L1 cells", *Biochem J.,* 330:1003–1008 (1998).*

Rubin, C.S., et al., "Development of Hormone Receptors and Hormonal Responsiveness in Vitro", *J. Biol. Chem.,* 253(20):7570–7578 (1978).*

Satoh, S., et al., "Use of Bismannose Photolabel to Elucidate Insulin–regulated GLUT4 Subcellular Trafficking Kinetics in Rat Adipose Cells", *J. Biol. Chem.,* 268(24):17820–17829 (1993).*

Scherer, P.E., et al., "A Novel Serum Protein Similar to C1q, Produced Exclusively in Adipocytes", *J. Biol. Chem.,* 270(45):26746–26749 (1995).*

Schürmann, A., et al., "Subcellular distribution and activity of glucose transporter isoforms GLUT1 and GLUT4 transiently expressed in COS–7 cells", *Biochim. Biophys. Acta.,* 1131(3):245–252 (1992).*

Shapiro, L. and Scherer P.E., "The crystal structure of a complement–1q family protein suggests an evolutionary link to tumor necrosis factor", *Curr. Biol.,* 8(6):335–338 (1998).*

Shibasaki, Y., et al., "Two glucose transporter isoforms are sorted differentially and are expressed in distinct cellular compartments", *Biochem J.,* 281:829–834 (1992).*

Slot, J.W., et al., "Immuno–localization of the Insulin Regulatable Glucose Transporter in Brown Adipose Tissue of the Rat", *J. Cell Biol.,* 113(1):123–135 (1991).*

Slot, J.W., et al., "Translocation of the glucose transporter GLUT4 in cardiac myocytes of the rat", *Proc. Natl. Acad. Sci. USA,* 88:7815–7819 (1991).*

Smith, G.A., et al., "The Tandem Repeat Domain in the *Listeria monocytogenes* ActA Protein Controls and Rate of Actin–based Motility, the Percentage of Moving Bacteria, and the Localization of Vasodilator–stimulated Phosphoprotein and Profilin", *J. Cell Biol.,* 135(3):647–660 (1996).*

Smith, R.M., et al., "Immuunoelectron microscopic demonstration of insulin–stimulated translocation of glucose transporters to the plasma membrane of isolated rat adipocytes and masking of the carboxyl–terminal epitope of intracellular GLUT4", *Proc. Natl. Acad. Sci USA,* 88:6893–6897 (1991).

Socolovsky, M., et al., "The Prolactin Receptor and Severely Truncated Erythropoietin Receptors Support Differentiation of Erythroid Progenitors", *J. Biol. Chem.,* 272(22):14009–14012 (1997).

Suzuki, K. and Kono, T., "Evidence that insulin causes translocation of glucose transport activity to the plasma membrane from an intracellular storage site", *Proc. Natl. Acad. Sci. USA,* 77(5):2542–2545 (1980).

Thorens, B. and Rot, J., "Intracellular targeting of GLUT4 in transfected insulinoma cells:evidence for association with constitutively recycling vesicles distinct from synaptophysin and insulin vesicles", *J. Cell Sci.,* 109:1311–1323 (1996).

Tokaka, M., et al., "Roles of insulin, guanosine 5'–[γ–thio] triphosphate and phorbol 12–myristate 13–acetate in signalling pathways of GLUT4 translocation", *Biochem J.,* 315:875–882 (1996).

Verhey, K.J., et al., "Identification of the Carboxy Terminus As Important for the Isoform–specific Subcellular Targeting of Glucose Transporter Proteins", *J. Cell Biol.,* 123(1):137–147 (1993).

Wang, Q., et al., "Protein Kinase B/Akt Participates in GLUT4 Translocation by Insulin in L6 Myoblasts", *Molecular and Cellular Biology,* 19(6):4008–4018 (1999).

Wei, M.L., et al., "GLUT4 and Transferrin Receptor Are Differentially Sorted Along the Endocytic Pathway in CHO Cells", *J. Cell Biol.,* 140(3):565–575 (1998).

Yang, J. and Holman, G., "Comparison of GLUT4 and GLUT1 Subcellular Trafficking in Basal and Insulin–stimulated 3T3–L1 Cells", *Biol. Chem.,* 268(7):4600–4603 (1993).

Yang, J., et al., "Development of an Intracellular Pool of Glucose Transporters in 3T3–L1 Cells",. *J. Biol. Chem.,* 267(15):10393–10399 (1992).

Yang, B. and Verkman, A.S., "Water and Glycerol Permeabilities of Aquaporins 1–5 and MIP Determined Quantitatively by Expression of Epitope–tagged Constructs in Xenopus Oocytes", *J. Biol. Chem.,* 272(26):16140–16146 (1997).

Yeh, J., et al., "Kinetic Analysis of Glucose Transporter Trafficking in Fibroblasts and Adipocytes", *Biochemistry,* 34(47):15523–15531 (1995).

Bogan, J.S. and Lodish, H.F., "A Novel Assay Indicates That The GLUT4 Recycling Pathway is Not Cell–Type Specific", Late Abstracts Poster Session, L65, The American Society for Cell Biology Thirty–Eighth Annual Meeting, Dec. 16, 1998.

* cited by examiner

```
1/1                                     31/11                                   61/21
ATG CCG TCG GGT TTC CAG CAG ATC GGC TCT GAA GAT GGG GAA CCC CCT CAG CAG CGA GTG ACT GGG ACA CTG GTC CTT GCT GTA TTC TCA
M   P   S   G   F   Q   Q   I   G   S   E   D   G   E   P   P   Q   Q   R   V   T   G   T   L   V   L   A   V   F   S
91/31                                   121/41                                  151/51
GCT GTG CTT GGC TCC CTT CAG TTT GGC TAT AAC ATT GGA GTC ATC AAC GCC CCA CAG AAA GTG ATT GAA CAG AGC TAC AAT GCA ACT TGG
A   V   L   G   S   L   Q   F   G   Y   N   I   G   V   I   N   A   P   Q   K   V   I   E   Q   S   Y   N   A   T   W
181/61                                  211/71                                  241/81
CTG GGT AGG CAG GGT CCT GCA GAG GAG CAA AAG CTT ATT TCT GAA GAG GAC TTG AAT GAA ATG GAG CAA AAG CTC ATT TCT GAA GAG GAC
L   G   R   Q   G   P   A   E   E   Q   K   L   I   S   E   E   D   L   N   E   M   E   Q   K   L   I   S   E   E   D
271/91                                  301/101                                 331/111
TTG AAT GAA ATG GAG CAA AAG CTC ATT TCT GAA GAG GAC TTG AAT GAA ATG GAG CAA AAG CTC ATT TCT GAA GAG GAC TTG AAT GAA ATG
L   N   E   M   E   Q   K   L   I   S   E   E   D   L   N   E   M   E   Q   K   L   I   S   E   E   D   L   N   E   M
361/121                                 391/131                                 421/141
GAG CAA AAG CTC ATT TCT GAA GAG GAC TTG AAT GAA ATG GAG AGC TTG GGC GAC CTC ACC ATG GAG CAA AAG CTC ATT TCT GAA GAG GAC
E   Q   K   L   I   S   E   E   D   L   N   E   M   E   S   L   G   D   L   T   M   E   Q   K   L   I   S   E   E   D
451/151                                 481/161                                 511/171
TTG AAC TCA AGA CCT CTT GAG CCT GCA GAG GAG CAA AAG CTT ATT TCT GAA GAG GAC TTG CTT AAG GGA CCC AGC TCC ATC CCT CCA GGC
L   N   S   R   P   L   E   P   A   E   E   Q   K   L   I   S   E   E   D   L   L   K   G   P   S   S   I   P   P   G
541/181                                 571/191                                 601/201
ACC CTC ACC ACC CTC TGG GCC CTC TCC GTG GCC ATC TTT TCC GTG GGC GGC ATG ATT TCC TCC TTC CTC ATT GGT ATC ATC TCT CAG TGG
T   L   T   T   L   W   A   L   S   V   A   I   F   S   V   G   G   M   I   S   S   F   L   I   G   I   I   S   Q   W
631/211                                 661/221                                 691/231
CTT GGA AGG AAA AGG GCC ATG CTG GTC AAC AAT GTC CTG GCG GTG CTG GGG GGC AGC CTC ATG GGC CTG GCC AAC GCT GCT GCC TCC TAT
L   G   R   K   R   A   M   L   V   N   N   V   L   A   V   L   G   G   S   L   M   G   L   A   N   A   A   A   S   Y
721/241                                 751/251                                 781/261
GAA ATG CTC ATC CTT GGA CGA TTC CTC ATT GGC GCC TAC TCA GGG CTG ACA TCA GGG CTG GTG CCC ATG TAC GTG GGG GAG ATT GCT CCC
E   M   L   I   L   G   R   F   L   I   G   A   Y   S   G   L   T   S   G   L   V   P   M   Y   V   G   E   I   A   P
811/271                                 841/281                                 871/291
ACT CAC CTG CGG GGC GCC CTG GGG ACG CTC AAC CAA CTG GCC ATT GTT ATC GGC ATT CTG ATC GCC CAG GTG CTG GGC TTG GAG TCC CTC
T   H   L   R   G   A   L   G   T   L   N   Q   L   A   I   V   I   G   I   L   I   A   Q   V   L   G   L   E   S   L
901/301                                 931/311                                 961/321
CTG GGC ACT GCC AGC CTG TGG CCA CTG CTC CTG GGC CTC ACA GTG CTA CCT GCC CTC CTG CAG CTG GTC CTG CTG CCC TTC TGT CCC GAG
L   G   T   A   S   L   W   P   L   L   L   G   L   T   V   L   P   A   L   L   Q   L   V   L   L   P   F   C   P   E
991/331                                 1021/341                                1051/351
AGC CCC CGC TAC CTC TAC ATC ATC CAG AAT CTC GAG GGG CCT GCC AGA AAG AGT CTG AAG CGC CTG ACA GGC TGG GCC GAT GTT TCT GGA
S   P   R   Y   L   Y   I   I   Q   N   L   E   G   P   A   R   K   S   L   K   R   L   T   G   W   A   D   V   S   G
1081/361                                1111/371                                1141/381
GTG CTG GCT GAG CTG AAG GAT GAG AAG CGG AAG CTG GAG CGT GAG CGG CCA CTG TCC CTG CTC CAG CTC CTG GGC AGC CGT ACC CAC CGG
V   L   A   E   L   K   D   E   K   R   K   L   E   R   E   R   P   L   S   L   L   Q   L   L   G   S   R   T   H   R
1171/391                                1201/401                                1231/411
CAG CCC CTG ATC ATT GCG GTC GTG CTG CAG CTG AGC CAG CAG CTC TCT GGC ATC AAT GCT GTT TTC TAT TAT TCG ACC AGC ATC TTC GAG
Q   P   L   I   I   A   V   V   L   Q   L   S   Q   Q   L   S   G   I   N   A   V   F   Y   Y   S   T   S   I   F   E
1261/421                                1291/431                                1321/441
ACA GCA GGG GTA GGC CAG CCT GCC TAT GCC ACC ATA GGA GCT GGT GTG GTC AAC ACA GTC TTC ACC TTG GTC TCG GTG TTG TTG GTG GAG
T   A   G   V   G   Q   P   A   Y   A   T   I   G   A   G   V   V   N   T   V   F   T   L   V   S   V   L   L   V   E
1351/451                                1381/461                                1411/471
CGG GCG GGG CGC CGG ACG CTC CAT CTC CTG GGC CTG GCG GGC ATG TGT GGC TGT GCC ATC CTG ATG ACT GTG GCT CTG CTC CTG CTG GAG
R   A   G   R   R   T   L   H   L   L   G   L   A   G   M   C   G   C   A   I   L   M   T   V   A   L   L   L   L   E
```

FIG. 8A

```
1441/481                                1471/491                                1501/501
CGA GTT CCA GCC ATG AGC TAC GTC TCC ATT GTG GCC ATC TTT GGC TTC GTG GCA TTT TTT GAG ATT GGC CCT GGC CCC ATT CCT TGG TTC
R   V   P   A   M   S   Y   V   S   I   V   A   I   F   G   F   V   A   F   F   E   I   G   P   G   P   I   P   W   F
1531/511                                1561/521                                1591/531
ATC GTG GCC GAG CTC TTC AGC CAG GGA CCC CGC CCG GCA GCC ATG GCT GTG GCT GGT TTC TCC AAC TGG ACG AGC AAC TTC ATC ATT GGC
I   V   A   E   L   F   S   Q   G   P   R   P   A   A   M   A   V   A   G   F   S   N   W   T   S   N   F   I   I   G
1621/541                                1651/551                                1681/561
ATG GGT TTC CAG TAT GTT GCG GAG GCT ATG GGG CCC TAC GTC TTC CTT CTA TTT GCG GTC CTC CTG CTG GGC TTC TTC ATC TTC ACC TTC
M   G   F   Q   Y   V   A   E   A   M   G   P   Y   V   F   L   L   F   A   V   L   L   L   G   F   F   I   F   T   F
1711/571                                1741/581                                1771/591
TTA AGA GTA CCT GAA ACT CGA GGC CGG ACG TTT GAC CAG ATC TCG GCT GCC TTC CAC CGG ACA CCC TCT CTT TTA GAG CAG GAG GTG AAA
L   R   V   P   E   T   R   G   R   T   F   D   Q   I   S   A   A   F   H   R   T   P   S   L   L   E   Q   E   V   K
1801/601                                1831/611                                1861/621
CCC AGC ACA GAA CTT GAG TAT TTA GGG CCA GAT GAG AAT GAC|CCG CGG GCC CGG GAT CCA CCG GTC GCC ACC|ATG GTG AGC AAG GGC GAG
P   S   T   E   L   E   Y   L   G   P   D   E   N   D  |P   R   A   R   D   P   P   V   A   T  |M   V   S   K   G   E
                                                       |end of GLUT4                           |beginning of GFP
1891/631                                1921/641                                1951/651
GAG CTG TTC ACC GGG GTG GTG CCC ATC CTG GTC GAG CTG GAC GGC GAC GTA AAC GGC CAC AAG TTC AGC GTG TCC GGC GAG GGC GAG GGC
E   L   F   T   G   V   V   P   I   L   V   E   L   D   G   D   V   N   G   H   K   F   S   V   S   G   E   G   E   G
1981/661                                2011/671                                2041/681
GAT GCC ACC TAC GGC AAG CTG ACC CTG AAG TTC ATC TGC ACC ACC GGC AAG CTG CCC GTG CCC TGG CCC ACC CTC GTG ACC ACC CTG ACC
D   A   T   Y   G   K   L   T   L   K   F   I   C   T   T   G   K   L   P   V   P   W   P   T   L   V   T   T   L   T
2071/691                                2101/701                                2131/711
TAC GGC GTG CAG TGC TTC AGC CGC TAC CCC GAC CAC ATG AAG CAG CAC GAC TTC TTC AAG TCC GCC ATG CCC GAA GGC TAC GTC CAG GAG
Y   G   V   Q   C   F   S   R   Y   P   D   H   M   K   Q   H   D   F   F   K   S   A   M   P   E   G   Y   V   Q   E
2161/721                                2191/731                                2221/741
CGC ACC ATC TTC TTC AAG GAC GAC GGC AAC TAC AAG ACC CGC GCC GAG GTG AAG TTC GAG GGC GAC ACC CTG GTG AAC CGC ATC GAG CTG
R   T   I   F   F   K   D   D   G   N   Y   K   T   R   A   E   V   K   F   E   G   D   T   L   V   N   R   I   E   L

2251/751                                2281/761                                2311/771
AAG GGC ATC GAC TTC AAG GAG GAC GGC AAC ATC CTG GGG CAC AAG CTG GAG TAC AAC TAC AAC AGC CAC AAC GTC TAT ATC ATG GCC GAC
K   G   I   D   F   K   E   D   G   N   I   L   G   H   K   L   E   Y   N   Y   N   S   H   N   V   Y   I   M   A   D
2341/781                                2371/791                                2401/801
AAG CAG AAG AAC GGC ATC AAG GTG AAC TTC AAG ATC CGC CAC AAC ATC GAG GAC GGC AGC GTG CAG CTC GCC GAC CAC TAC CAG CAG AAC
K   Q   K   N   G   I   K   V   N   F   K   I   R   H   N   I   E   D   G   S   V   Q   L   A   D   H   Y   Q   Q   N
2431/811                                2461/821                                2491/831
ACC CCC ATC GGC GAC GGC CCC GTG CTG CTG CCC GAC AAC CAC TAC CTG AGC ACC CAG TCC GCC CTG AGC AAA GAC CCC AAC GAG AAG CGC
T   P   I   G   D   G   P   V   L   L   P   D   N   H   Y   L   S   T   Q   S   A   L   S   K   D   P   N   E   K   R
2521/841                                2551/851                                2581/861
GAT CAC ATG GTC CTG CTG GAG TTC GTG ACC GCC GCC GGG ATC ACT CTC GGC ATG GAC GAG CTG TAC AAG TAA
D   H   M   V   L   L   E   F   V   T   A   A   G   I   T   L   G   M   D   E   L   Y   K   *
```

FIG. 8B

SEQUENCE LISTING

<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<223> OTHER INFORMATION: myc epitope

<400> SEQUENCE: 1

Glu Gln Lys Leu Ile Ser Glu Glu Asp Leu
1 5 10

<210> SEQ ID NO 2
<211> LENGTH: 20
<212> TYPE: DNA
<213> ORGANISM: Artificial Sequence -continued
<220> FEATURE:
<223> OTHER INFORMATION: primer

<400> SEQUENCE: 2
gacatttgac cagatctcgg 20

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
ggcccgcggg tcattctcat ctggccc 27

<210> SEQ ID NO 4
<211> LENGTH: 36
<212> TYPE: DNA
<213> ORGANISM: Artificial Sequence
<220> FEATURE:
<223> OTHER INFORMATION: primer

<400> SEQUENCE: 4
ccggccgaat tcatgccgtc gggtttccag cagatc 36

<210> SEQ ID NO 5
<211> LENGTH: 55
<212> TYPE: DNA
<213> ORGANISM: Artificial Sequence
<220> FEATURE:
<223> OTHER INFORMATION: primer

<400> SEQUENCE: 5
cttcagaaat aagcttttgc tcctctgcag gaccctgcct acccagccaa gttgc 55

<210> SEQ ID NO 6
<211> LENGTH: 44
<212> TYPE: DNA
<213> ORGANISM: Artificial Sequence
<220> FEATURE:
<223> OTHER INFORMATION: primer

<400> SEQUENCE: 6
ccatcgattt aaagctatgg agcaaaagct tatttctgaa gagg 44

<210> SEQ ID NO 7
<211> LENGTH: 58
<212> TYPE: DNA
<213> ORGANISM: Artificial Sequence
<220> FEATURE:
<223> OTHER INFORMATION: primer

<400> SEQUENCE: 7
cagaaataag cttttgctcc tctgcaggct caagaggtct tgagttcaag tcctcttc 58

<210> SEQ ID NO 8
<211> LENGTH: 2592
<212> TYPE: DNA
<213> ORGANISM: Artificial Sequence
<220> FEATURE:
<223> OTHER INFORMATION: modified GLUT4 containing myc tag sequences

<400> SEQUENCE: 8
atgccgtcgg gtttccagca gatcggctct gaagatgggg aaccccctca gcagcgagtg 60

-continued

```
actgggacac tggtccttgc tgtattctca gctgtgcttg gctcccttca gtttggctat    120
aacattggag tcatcaacgc ccccacagaaa gtgattgaac agagctacaa tgcaacttgg    180
ctgggtaggc agggtcctgc agaggagcaa aagcttattt ctgaagagga cttgaatgaa    240
atggagcaaa agctcatttc tgaagaggac ttgaatgaaa tggagcaaaa gctcatttct    300
gaagaggact tgaatgaaat ggagcaaaag ctcatttctg aagaggactt gaatgaaatg    360
gagcaaaagc tcatttctga agaggacttg aatgaaatgg agagcttggg cgacctcacc    420
atggagcaaa agctcatttc tgaagaggac ttgaactcaa gacctcttga gcctgcagag    480
gagcaaaagc ttatttctga agaggacttg cttaagggac ccagctccat ccctccaggc    540
accctcacca ccctctgggc cctctccgtg gccatctttt ccgtgggcgg catgatttcc    600
tccttcctca ttggtatcat ctctcagtgg cttggaagga aaagggccat gctggtcaac    660
aatgtcctgg cggtgctggg gggcagcctc atgggcctgg ccaacgctgc tgcctcctat    720
gaaatgctca tccttggacg attcctcatt ggcgcctact cagggctgac atcagggctg    780
gtgcccatgt acgtgggggga gattgctccc actcacctgc ggggcgccct ggggacgctc    840
aaccaactgg ccattgttat cggcattctg atcgcccagg tgctgggctt ggagtccctc    900
ctgggcactg ccagcctgtg gccactgctc ctgggcctca cagtgctacc tgccctcctg    960
cagctggtcc tgctgccctt ctgtcccgag agcccccgct acctctacat catccagaat   1020
ctcgaggggc ctgccagaaa gagtctgaag cgcctgacag gctgggccga tgtttctgga   1080
gtgctggctg agctgaagga tgagaagcgg aagctggagc gtgagcggcc actgtccctg   1140
ctccagctcc tgggcagccg tacccaccgg cagcccctga tcattgcggt cgtgctgcag   1200
ctgagccagc agctctctgg catcaatgct gttttctatt attcgaccag catcttcgag   1260
acagcagggg taggccagcc tgcctatgcc accataggag ctggtgtggt caacacagtc   1320
ttcaccttgg tctcggtgtt gttggtggag cgggcggggc gccggacgct ccatctcctg   1380
ggcctggcgg gcatgtgtgg ctgtgccatc ctgatgactg tggctctgct cctgctggag   1440
cgagttccag ccatgagcta cgtctccatt gtggccatct ttggcttcgt ggcatttttt   1500
gagattggcc ctggccccat tccttggttc atcgtggccg agctcttcag ccagggaccc   1560
cgcccggcag ccatggctgt ggctggtttc tccaactgga cgagcaactt catcattggc   1620
atgggtttcc agtatgttgc ggaggctatg ggccctacg tcttccttct atttgcggtc   1680
ctcctgctgg gcttcttcat cttcaccttc ttaagagtac ctgaaactcg aggccggacg   1740
tttgaccaga tctcggctgc cttccaccgg acaccctctc ttttagagca ggaggtgaaa   1800
cccagcacag aacttgagta tttagggcca gatgagaatg acccgcgggc ccgggatcca   1860
ccggtcgcca ccatggtgag caagggcgag gagctgttca ccggggtggt gcccatcctg   1920
gtcgagctgg acggcgacgt aaacggccac aagttcagcg tgtccggcga gggcgagggc   1980
gatgccacct acggcaagct gaccctgaag ttcatctgca ccaccggcaa gctgcccgtg   2040
ccctggccca ccctcgtgac caccctgacc tacggcgtgc agtgcttcag ccgctacccc   2100
gaccacatga agcagcacga cttcttcaag tccgccatgc ccgaaggcta cgtccaggag   2160
cgcaccatct tcttcaagga cgacggcaac tacaagaccc gcgccgaggt gaagttcgag   2220
ggcgacaccc tggtgaaccg catcgagctg aagggcatcg acttcaagga ggacggcaac   2280
atcctggggc acaagctgga gtacaactac aacagccaca acgtctatat catggccgac   2340
aagcagaaga acggcatcaa ggtgaacttc aagatccgcc acaacatcga ggacggcagc   2400
gtgcagctcg ccgaccacta ccagcagaac acccccatcg gcgacggccc cgtgctgctg   2460
```

-continued

```
cccgacaacc actacctgag cacccagtcc gccctgagca aagaccccaa cgagaagcgc   2520

gatcacatgg tcctgctgga gttcgtgacc gccgccggga tcactctcgg catggacgag   2580

ctgtacaagt aa                                                       2592
```

METHOD OF MEASURING PLASMA MEMBRANE TARGETING OF GLUT4

This application claims benefit of Provisional application No. 60/154,078, filed Sep. 15, 1999, which claims benefit of No. 60/138,237, filed Jun. 9, 1999.

BACKGROUND OF THE INVENTION

Insulin resistance is important in the development of adult-onset diabetes mellitus and several lines of evidence indicate that an initial defect in adult onset diabetes is reduced insulin-stimulated recruitment of GLUT4 glucose transporter from a sequestered intracellular site to the cell surface in muscle and fat cells. An increase in cell surface (plasma membrane) GLUT4 amount allows for an increased rate of facilitated diffusion of glucose into cells. Presently available methods of determining or measuring GLUT4 translocation, such as methods involving assessment of $^3$H 2-deoxyglucose uptake, cell fractionation, counting radioactivity that binds to adherent cells on a multiwell plate, plasma membrane sheet assays and immunofluorescence microscopy are laborious and/or only semiquantitative. It would be of considerable interest to be able to measure GLUT4 glucose transporter protein translocation easily and quantitatively.

SUMMARY OF THE INVENTION

The present invention relates to a method of assessing translocation of a protein of interest in cells which occurs when the cells are exposed to a condition or treated in such a manner that a protein that is sequestered at an intracellular location moves (is translocated) to the cell surface (plasma membrane) or, alternatively, a protein at the cell surface moves (is translocated) to an intracellular location. It also relates to a method of determining whether a condition or set of conditions to which cells are exposed or contacted alters (induces, enhances or inhibits) translocation of a protein of interest known to undergo translocation under certain conditions. The protein whose movement is being assessed is referred to as a protein of interest. The method is carried out using a modified form of the protein of interest, referred to as a modified protein of interest or a reporter protein. The reporter protein is the protein of interest modified in such a manner that it comprises one or more tags that allow quantification of relative amounts of the protein that are at the cell surface and of the total amounts of the protein in the cells. For example, it can comprise one or more intracellular tag(s) and one or more extracellular tag(s). The extracellular tag(s) and the intracellular tag(s) are distinct tags; that is, they are different tags that can be detected separately/distinguished from one another (e.g., two fluorescent tags detectable at different wavelengths). The reporter protein moves within the cells in essentially the same way as the protein of interest. The intracellular tag e.g., an intracellular fluorescent tag corresponds to the total protein of interest in the cell and does not change in quantity depending on the location of the reporter protein in the cell. The intracellular tag is fused in-frame in the DNA or RNA sequence that encodes the protein. The extracellular tag (e.g., an epitope(s) or radioactive label) is detectable only if the tag is extracellular, since the detector used is one that is unable to (does not) cross the cell membrane; the detector can be, for example, an antibody or other compound that recognizes (binds) the extracellular tag. Thus, the extent to which the extracellular tag is detectable (e.g., the intensity of fluorescence due to the epitope tag(s)) is indicative of the extent to which the protein of interest is present at the cell membrane. The intracellular tag can be any fluorescent tag, such as Green Fluorescent Protein (GFP), Blue Fluorescent Protein (BFP), Red Fluorescent Protein (RFP) or a sequence of amino acids designed to bind a molecule that has fluorescent, radioactive, or other detectable characteristics. The extracellular tag is generally an epitope tag or tags that is recognized by an antibody. The antibody can be monoclonal or polyclonal and can itself be detectably labeled (e.g., fluorescently labeled) or can be recognized (bound) by a detectably labeled antibody (a labeled secondary antibody). For example, the epitope tag(s) can be recognized by a primary or secondary antibody labeled with phycoerythrin (PE). Any pair of fluorescent labels can be used, as long as they are detectable at distinct wavelengths (different wavelengths). If there are two or more intracellular tags and/or two or more extracellular tags, it is only necessary that there are distinct detectable differences (such as distinct/different wavelengths) that correspond to surface protein of interest and total protein of interest. Alternatively radioactive, colorimetric, luminescent or other detection strategies may be used. The only requirements are that 1) the two tags can be detected individually and each can be quantified and 2) the addition of tag(s) does not substantially alter trafficking of the protein of interest with cells.

The extent of translocation of the protein of interest is assessed by culturing or treating cells that contain the reporter protein (referred to as test cells) under a condition (s) to be assessed for their effects on translocation of the protein of interest to the cell membrane; determining the intensity of the intracellular tag (e.g., intensity of fluorescence of an intracellular tag, such as GFP, RFP or BFP) and the intensity of the extracellular tag (e.g., by measuring the intensity of fluorescence of epitope tag(s) by means of fluorescently labeled antibodies); calculating the proportion or fraction of and determining a value corresponding to the total cellular modified protein of interest that is present at the cell surface and comparing the resulting proportion with the corresponding proportion calculated for control cells. Control cells are the same type of cells as the test cells and are cultured or handled in the same manner as are the test cells, except that control cells are not cultured or treated under the conditions being assessed for their effects on translocation to the cell membrane. For example, if test cells are cultured in the presence of a hormone or growth factor, control cells are cultured under the same conditions as the test cells, except in the absence of the hormone or growth factor. Two measurements (such as fluorescence at two different wavelengths), F1 and F2, correspond, respectively, to cell surface protein of interest and total protein of interest in the cells. If the proportion of protein of interest at the cell membrane to total protein of interest is greater for test cells than for control cells, translocation has occurred in the test cells and the condition under which the test cells were cultured or treated (e.g., in the presence of a hormone or growth factor) is a condition that causes or enhances translocation from an intracellular location to the cell membrane. Translocation from the cell membrane to an intracellular location for a protein of interest can also be assessed using the modified protein of interest and the method of the present invention.

In a particular embodiment, the protein whose translocation is assessed is GLUT4 and the modified protein of interest is modified GLUT4, also referred to as GLUT4 reporter, which includes an intracellular tag and at least one, and preferably multiple, extracellular tag(s). For example, the intracellular tag is GFP, RFP or BFP and the extracellular tag(s) are epitope tag(s), which can be detected using a fluorescent or a radioactive label. The ratio of protein of interest at the cell membrane (F1) to total protein of interest in test cells (F2) is compared to the ratio of protein of interest at the cell membrane (F1) to total protein of interest in the control cells, (F2). If the proportion is greater in the test cells is greater than the control cells, the condition(s) is an enhancer of/causes translocation to the cell membrane.

As described below with specific reference to GLUT4, preferably three sets of values, each consisting of fluorescence intensities at two distinct wavelengths, are determined in the method of assessing change in the proportion of the protein of interest that is present at the plasma membrane (and, thus, the extent to which translocation has occurred). The two wavelengths, F1 and F2, correspond, respectively, to cell surface (plasma membrane) protein of interest and total protein of interest in the cell. The three sets of values are F1 and F2 in control cells, F1 and F2 in background cells and F1 and F2 in test cells. In some cases, separate background sets of values may be required for tests and for control cells so that there are four sets of values in all. Cell surface protein of interest can be measured by a fluorophore (e.g., PE) coupled to an antibody that binds to externalized epitope tag(s), such as myc epitope tag(s), but not to intracellular myc epitope tag, or by a secondary fluorophore-bearing antibody that recognizes a primary antibody that recognizes the myc epitope. The three sets of values are as described below with specific reference to GLUT4.

Insulin stimulates glucose uptake in muscle and adipose tissues by causing translocation of the GLUT4 glucose transporter from a sequestered, intracellular compartment to the plasma membrane. Described herein is a novel assay to measure changes in the proportion (fraction) of total GLUT4 present at the plasma membrane of cultured cells expressing a reporter protein, based on measurement of a detectable tag corresponding to cell surface amount of GLUT4 and measurement of a second (different) detectable tag corresponding to total amount of GLUT4 in the cells. The two tags can both be, for example, fluorescent tags that are detectable at different wavelengths or two different types of tags, such as a fluorescent tag corresponding to total cell GLUT4 and a radioactive label or an epitope(s) corresponding to GLUT4 at the cell surfaces. Various types of measurement can be used to detect the two tags. For example, if fluorescence is used to detect the two tags, then flow cytometry can be used to measure the tags quantitatively and on a cell-by-cell basis. This assay has been used to demonstrate that insulin stimulates GLUT4 translocation with identical kinetics at all times during differentiation of a subline of 3T3-L1 adipocytes, even in undifferentiated, confluent fibroblasts. This effect is invariably blocked by phosphatidylinositol-3-kinase inhibitors. In all cases, the reporter is reinternalized after insulin removal, and recycles upon insulin readdition.

As also described herein, insulin has been shown to trigger GLUT4 externalization in Chinese hamster ovary (CHO) cells, with initial kinetics and magnitude identical to those in 3T3-L1 adipocytes, when the CHO cells are cultured under the same conditions as those under which the 3T3-L1 adipocytes are cultured. Thus, CHO cells, 3T3-L1 fibroblasts, and 3T3-L1 adipocytes all contain an intracellular recycling compartment to which GLUT4 is targeted, and that is rapidly mobilized upon insulin addition.

Described herein is an assay for measuring the effects of conditions on translocation (movement of a protein of interest from an intracellular location to the plasma membrane or from the plasma membrane to an intracellular location). In a specific embodiment, the invention is an assay for measuring the effects of conditions, such as the presence of insulin and other stimulators, on targeting of GLUT4 to the plasma membrane of cells and, thus, for measuring their effects on glucose uptake. Also described herein is a method of assessing the effect of a drug on translocation of a protein of interest, such as GLUT4, from an internal (intracellular) location to the plasma membrane or from the plasma membrane to an intracellular location. The method is useful to identify drugs which alter translocation of the protein of interest. Of particular interest is a method of identifying drugs that alter GLUT4 translocation, such as drugs that increase the fraction of GLUT4 in the plasma membrane (in the absence and/or presence of insulin) or that enhance the effect of insulin on GLUT4 translocation to the plasma membrane and, thus, are useful in enhancing uptake of glucose into cells, since stimulation of glucose transport by insulin requires translocation of GLUT4 to the plasma membrane. An increase in GLUT4 at the cell membrane allows for a rapid increase in the rate of facilitated diffusion of glucose into the cell. Such drugs are useful, for example, in treating insulin resistance, such as occurs in adult-onset diabetes, obesity and polycystic ovary syndrome. Modified protein of interest; DNA encoding modified protein of interest; expression vectors, cells and cell lines containing DNA encoding modified protein of interest; and expression vectors, cells and cell lines expressing DNA encoding modified protein of interest are also described. Modified GLUT4 glucose transporter protein; DNA encoding modified GLUT4;expression vectors (e.g., retroviral vectors, such as replication-deficient retroviral vectors, adenoviral vectors and other expression vectors for eukaryotic cells), cells and cell lines containing DNA modified GLUT4; and expression vectors and cells and cell lines expressing modified GLUT4 are particular embodiments of this invention. They are useful in the methods described herein.

Described herein are the production of a DNA construct encoding one embodiment of modified GLUT4 and cells in which modified GLUT4 was expressed. Modified GLUT4 is GLUT4 protein which comprises at least one (one or more) detectable tag, such as at least one epitope tag in an extracellular domain and a detectable tag, such as a fluorescent tag, in an intracellular domain. The intracellular tag is fused in-frame in the modified GLUT4 protein. The epitope tag is, for example, present in the first extracellular domain of GLUT4 and is, for example, a myc epitope or myc epitopes. The fluorescent tag is, for example, GFP or BFP. In one embodiment of the construct described herein, GFP provides an internal control for the amount of protein present. For example, the externalized epitope tag is detected with a "red" fluorescent antibody and GFP is detected using "green" fluorescence. Translocation can, as a result, be measured by the increase in the ratio of "red " fluorescence to "green" fluorescence. This ratio can be measured, for example, using flow cytometry or a fluorescent plate reader. Translocation of modified GLUT4 is detected using an antibody which binds the epitope tag; the bound antibody can be identified by means of a labeled (e.g., fluorescently labeled) second antibody which binds the first antibody. Alternatively, the epitope binding antibody can itself be labeled, such as fluorescently labeled. In either case, detection of the fluorescent label is carried out using known methods, such as flow cytometry, fluorescent plate reader or microscopy. The eukaryotic (e.g., mammalian, avian, reptilian) cells in which modified GLUT4 is expressed can be primary cells or a cell line, such as mouse, human, hamster, rat, rabbit, guinea pig, monkey, dog, cat or human primary cells or cell lines derived from one of these sources.

BRIEF DESCRIPTION OF THE DRAWINGS

The foregoing and other objects, features and advantages of the invention will be apparent from the following more particular description of preferred embodiments of the invention, as illustrated in the accompanying drawings.

The file of this patent contains at least one drawing in color. Copies of this patent with color drawing(s) will be provided by the Patent and Trademark office upon request and payment of the necessary fee.

FIG. 1A is a schematic representation of a modified GLUT4 reporter containing myc epitope tags in the first exofacial loop and GFP in frame at the carboxy terminus.

FIG. 1B shows results of time-lapse video fluorescence microscopy of a 3T3-L1 adipocyte expressing the reporter which demonstrates GFP fluorescence in the perinuclear location characteristic of GLUT4.

FIG. 1C shows results of the use of flow cytometry to quantitate the insulin-stimulated change in the proportion of GLUT4 at the plasma membrane of 3T3-L1 adipocytes expressing the reporter protein. PE and GFP fluorescence intensities are plotted on the vertical and horizontal axes of the dotplots presented. Note that both scales are logarithmic. Compared to the fluorescence of unstained cells (background, shown in blue), basal (stained for cell-surface myc, shown in red) and insulin-stimulated (80 nM, 10 min; stained for cell-surface myc, shown in green) populations have increased PE fluorescence with no change in GFP fluorescence. The three panels allow direct comparison of each pair of samples; the basal and background populations overlap significantly (left panel), corresponding to minimal GLUT4 on the surface of basal cells. In contrast, the insulin-stimulated cells are well separated from both background and basal populations (center and right panels, respectively). In this experiment, insulin caused a 5.0-fold increase in PE fluorescence, with no change in GFP fluorescence, corresponding to a 5.0-fold increase in the proportion of total GLUT4 present at the cell surface. A small fraction of cells (2–3%) in the basal and insulin-stimulated samples are highly PE-fluorescent (e.g. dashed box in left panel); these are fragmented or permeablized cells that do not significantly affect the median fluorescence intensities of the entire populations.

FIG. 2A shows results of assessment of 10 cm dishes of cells at the indicated days of differentiation.

FIG. 2B shows results of phase contrast (upper left) and bright field (upper right and lower left and right) microscopy of cells at the indicated days of differentiation. Scale bar, 50 m.

FIG. 3A shows results of measurement of confluent 3T3-L1 fibroblasts ('Day 0') or 3T3-L1 cells that had undergone differentiation for various lengths of time and were stimulated or not with insulin (160 nM, 10 min.), and changes in the proportion of GLUT4 reporter present at the cell surface, using flow cytometry as described in the text. Some samples were treated with either 100 nM wortmannin or 50 M LY294002 for 40 min. prior to insulin addition, as noted. The amount of the reporter within each cell varies during 3T3-L1 differentiation, and is increased approximately 3-fold on Days 2 and 4 (not shown). This was attributed to increased activity of the retroviral promoter as the cells undergo clonal expansion at the onset of adipocyte differentiation, especially since increased expression of the reporter is also observed in preconfluent, dividing fibroblasts. Because the assay measures changes in the ratio of cell-surface to total GLUT4, rather than in the absolute amount of cell-surface GLUT4, the data presented are internally controlled for this variation and data from different days of differentiation can be meaningfully compared. In all instances, insulin stimulates GLUT4 exocytosis and this effect is blocked by either of the two PI3K inhibitors.

In FIG. 3B dotplots demonstrating insulin-stimulated GLUT4 exocytosis in confluent 3T3-L1 fibroblasts are presented. As in FIG. 1C, PE and GFP fluorescence intensities correspond to cell surface and total GLUT4, respectively, and are plotted logarithmically on the vertical and horizontal axes. Background (unstained) cells are shown in blue, basal and insulin-stimulated (80 nM, 5 min.) populations are shown in red and green, respectively. In this experiment, insulin stimulated a 4.4-fold increase in the proportion of total GLUT4 present at the cell surface.

FIGS. 8A and 8B are the nucleic acid sequence of DNA that encodes modified GLUT4 (SEQ ID NO.: 8) and the amino acid sequence of modified GLUT4. The myc tag sequences are underlined, and the end of the GLUT4 sequence and the beginning of the GFP sequence are indicated. There are no amino acid residues between the two sequences.

DETAILED DESCRIPTION OF THE INVENTION

Figure 1A:
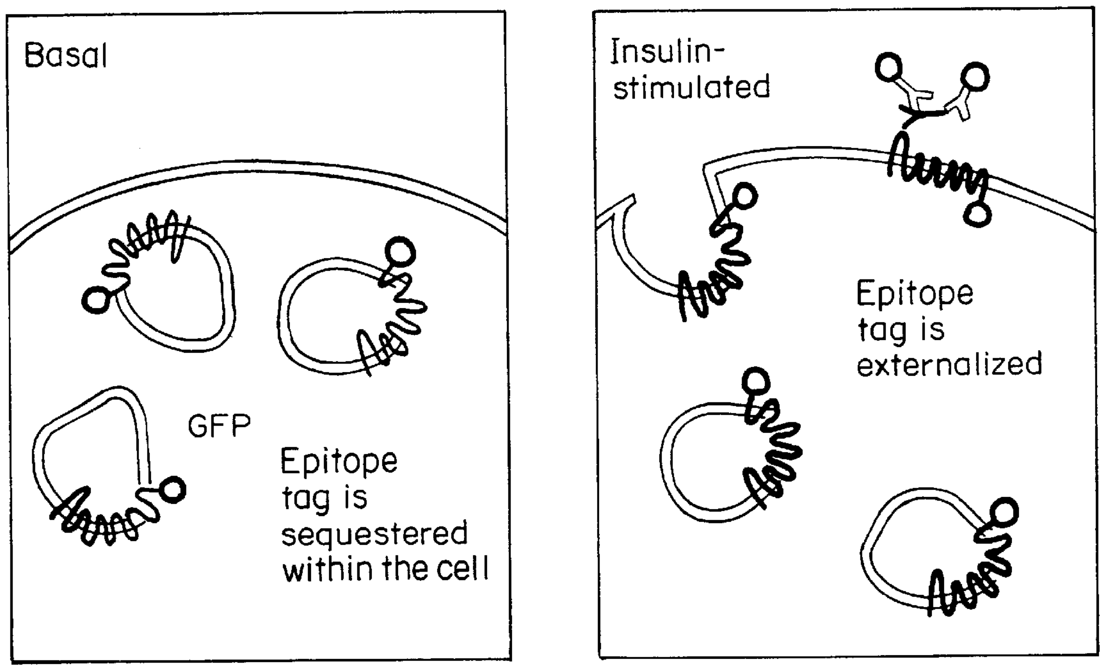
FIGS. 1A–1C show aspects of an assay for changes in the proportion of GLUT4 at the plasma membrane.

The present invention relates to a method of measuring or assessing translocation (movement from an intracellular location to the cell surface (plasma membrane) or from the cell surface to an intracellular location) of a protein of interest in eukaryotic cells, in response to a condition(s) or stimulus that triggers translocation of the protein. It also relates to a method of measuring the effects of subjecting eukaryotic cells to the presence or absence of one or more conditions on the proportion of the protein of interest at the cell surface or, conversely, on the proportion of the protein of interest located intracellularly. It further relates to a method of identifying drugs that alter (enhance or reduce) translocation of the protein of interest and to drugs that alter translocation. A further subject of this invention are modified proteins of interest, which comprise the protein of interest, an intracellular tag(s) or reporter(s) and an extracellular tag(s). The modified protein of interest translocates in a manner substantially the same as the protein of interest and can be "followed" in cells through assessment of the intracellular tag—which corresponds to the total protein of interest in the cell—and of the extracellular tag—which is indicative of the extent to which the protein of interest is present at the cell membrane. Calculation of the fraction or proportion of total modified protein of interest at the cell membrane (or at an intracellular location) in test cells and in control cells and comparison of the resulting values shows if the presence or absence of the condition(s) or stimulator(s) alters (enhances or reduces) translocation, as described in greater detail herein. Thus, such modified proteins of interest are useful in the methods of the present invention. In specific embodiments, the protein of interest is, for example, GLUT4 protein, Aquaporin-2 (AQP2), Cystic Fibrosis Transmembrane Conductance Regulator (CFTR) or gastric H+/K+ ATPase.

In a specific embodiment, the present invention relates to a method of measuring the effects of subjecting cells to the presence or absence of one or more different conditions on the proportion of GLUT4 protein on the cell surface, Such conditions may result in translocation of GLUT4 protein from its intracellular location to the cell (plasma) membrane or vice versa (from the plasma membrane to an intracellular location). For example, when the condition is the presence of insulin, translocation is assessed in the absence of insulin and in its presence and the proportion (fraction) of GLUT4 on the cell surface (relative to total GLUT4 in the cell) in the absence of insulin is compared with the proportion of GLUT4 on the cell surface in the presence of insulin.

Alternatively, more than one condition can be used to test their effects on translocation. For example, the effect of the presence or absence of insulin can be tested in the presence or absence of a second condition, such as the presence or absence of high glucose concentration or other conditions that mimic insulin resistance (e.g., increased concentrations of the fatty acids, tumor necrosis factor (TNF-α or alteration in the level of another hormone), Thus, the effects of the presence or absence of several, independent conditions on targeting of GLUT4 to the plasma membrane can be assessed using the method and cells of the present invention. As used herein, the term "condition" encompasses a single condition (e.g., the presence of insulin) or a combination of conditions (e.g., the presence of insulin and high glucose concentration or the presence of insulin, high glucose concentration and a candidate drug), as discussed further herein.

The method can be carried out in any type of eukaryotic cell (e.g., mammalian, including human, hamster, mouse, rat, avian, reptilian) in which GLUT4 exocytosis (translocation) is stimulated by insulin. Cells can be differentiated or undifferentiated and in specific embodiment, are adipocytes, fibroblasts or muscle cells, such as 3T3-L1 cells (undifferentiated or differentiated) or Chinese Hamster Ovary (CHO) cells.

In one embodiment of the present method, translocation of GLUT4 glucose transporter protein from its intracellular location to the plasma membrane upon treatment by conditions that cause GLUT4 protein to undergo translocation (e.g., the presence of insulin, another hormone, decreased glucose concentration or conditions which mimic insulin resistance, such as high glucose levels or increased tumor necrosis factor -α concentration (TNF-α), high non-esterified fatty acid concentration and other conditions TNF-α) is assessed. Translocation is evidenced by an increase in the proportion of GLUT4 at the plasma membrane, relative to total GLUT4. In an alternative embodiment, movement of GLUT4 from the plasma membrane to an intracellular location is assessed. This movement is evidenced by a decrease in the proportion of GLUT4 at the plasma membrane, relative to total GLUT4.

Thus, the present invention provides a method of detecting and/or quantifying changes in the proportion of GLUT4 at the plasma membrane of cells under varying conditions and of determining conditions under which translocation to or from the plasma membrane occurs. As used herein, the term "translocation" includes both movement from an intracellular location to the plasma membrane and movement from the plasma membrane to an intracellular location. The method is useful to identify drugs or agents that alter, particularly enhance, translocation of intracellular GLUT4 to the plasma membrane and, thus, to identify drugs useful in treating insulin-resistant diabetes (also referred to as adult onset, noninsulin dependent or type II diabetes) or other insulin-resistant conditions or states, such as obesity and polycystic ovary syndrome.

Translocation of GLUT4 is assessed using a modified GLUT4 protein, which is also the subject of the present invention. The modified GLUT4 is GLUT4 protein that includes at least one (one or more) detectable tags, such as an epitope(s) or other label, in an extracellular domain and a detectable tag or tags, such as a or fluorescent tag (e.g., a fluorescent protein) in an intracellular domain. The first epitope tag(s) can be from any protein other than GLUT4, or can be from GLUT4 itself if it can be detected specifically when outside of a cell, provided that whatever epitope tag(s) is used, it does not interfere with translocation of the modified GLUT4 protein. The epitope tag need not be detected using an antibody. It can, for instance, have enzymatic activity that allows detection only when it is extracellular. The second detectable tag(s) corresponds to total cellular GLUT4. Typically, the tag is in an intracellular region of the modified GLUT4 protein, but it can be present in an extracellular region, provided that its detectable characteristic (e.g., fluorescence) is not altered by changes in conditions (e.g., pH, ionic concentrations) which occur when the modified protein moves to the cell surface. The second detectable tag (e.g., the fluorophore, such as GFP, RFP or BFP) corresponds to total GLUT4 in the cell and does not change in quantity depending on the location of the protein within the cell. In contrast, the first epitope tag causes fluorescence only if it is extracellular, since only then is it recognized by an antibody (that cannot cross the cell membrane and, thus, can recognize only extracellular epitopes). The antibody that recognizes the epitope can itself be detectably (e.g., fluorescently) labeled or can, in turn, be recognized by a secondary antibody that carries a detectable label (e.g., a fluorophore). In those instances in which modified GLUT4 is detected in an assay by means of fluorescence, the two fluorescent labels (one to detect the epitope(s) in the first extracellular domain and one present in an intracellular domain) used must be different (detectable at different wavelengths). For example, if a fluorescently-labeled antibody is used to detect the epitope tag(s) of modified GLUT4, the fluorescent moiety on the antibody must be detectable at a wavelength different from the wavelength at which the fluorescent tag (e.g., GFP or BFP) in the intracellular domain of GLUT4 is detected.

One example of modified GLUT4 protein of the present invention is the protein encoded by DNA of SEQ ID NO.: 8. Other examples of modified GLUT4 protein of the present invention include proteins which are sufficiently similar (e.g., at least 90% identical) in sequence to that encoded by DNA of SEQ ID NO.: 8 that they move to and from the cell surface in a manner similar to the way in which GLUT4 moves and are distributed within cells in a similar pattern as the distribution of GLUT4. Modified GLUT4 can be produced by a variety of methods, such as by recombinant DNA methods (e.g., production of DNA or RNA encoding all or a portion of the modified protein, followed by its expression by an appropriate expression vector or system and, if necessary, further modification or joining of portions/components, such as the intracellular tag(s) and/or epitope tag(s) to produce modified GLUT4). It can also be produced by modifying GLUT4 protein itself, such as by the addition of a fluorescent or other detectable tag and one or more epitope tags.

In specific embodiments, at least one epitope tag is present in the first extracellular domain (also referred to as the first exofacial loop) of modified GLUT4 and is, for example, a myc epitope that is an amino acid sequence comprising the amino acid residues EQKLISEEDL (SEQ ID NO.:1) (as represented by standard one letter codes) which is recognized by an anti-c-myc monoclonal antibody such as clone 9E10. The 9E10 hybridoma cell line, which produces this antibody, is available through the American Type Culture Collection (Rockville, Md.). The myc epitope can be identified by an anti-myc antibody (e.g., a detectably labeled anti-myc antibody), a detectably labeled antibody that recognizes an anti-myc antibody (a secondary antibody) or can itself be detectably labeled (e.g., by fluorescence or by addition of one member of a pair of ligands, such as biotin and avidin). The modified GLUT4 protein can comprise more than one epitope tag. Any number of epitope tags can be included, provided that the resulting modified GLUT4 undergoes translocation in a manner similar to that in which GLUT4 undergoes translocation. For example, any number of epitope tags, from one to 15 or 20, can be included. In a specific embodiment, seven epitope tags, such as seven myc tags, are included in the first exofacial loop of GLUT4. Alternatively, six, eight, nine or ten epitope tags can be included. The detectable tag in an intracellular domain (e.g., at the carboxy terminus) of GLUT4 can be any detectable tag, such as a fluorescent protein, provided that its presence does not interfere with translocation of modified GLUT4. In particular embodiments exemplified herein, the fluorescent tag in an intracellular domain of GLUT4 is GFP, RFP or BFP, which is present at the carboxy terminus of the modified GLUT4 protein.

In one embodiment described herein, modified GLUT4 comprises one myc epitope tag in an extracellular domain and either GFP or BFP at the carboxy terminus of GLUT4. In a further embodiment, modified GLUT4 comprises two to ten and, specifically, seven myc epitope tags in the first extracellular domain and either GFP or BFP at the carboxy terminus of GLUT4. Alternatively, GFP or BFP is present elsewhere within an intracellular domain of GLUT4.

DNA encoding modified GLUT4 protein is also the subject of the present invention, as are vectors (e.g., retroviral, adenoviral vectors, and other eukaryotic expression vectors, such as replication-deficient forms of the viruses) from which the DNA is expressed in cells containing the vectors. DNA used to produce modified GLUT4 comprises DNA encoding GLUT4 protein in which an epitope tag or tags is present in an extracellular domain and a detectable tag, such as a fluorescent tag, is present in an intracellular domain, such as at the carboxy terminus. The DNA encodes, in one embodiment, modified GLUT4 in which at least one myc epitope tag is in the first extracellular domain and a fluorescent tag, such as GFP or BFP, is present in an intracellular domain. In a specific embodiment, DNA of the present invention encodes modified GLUT4 protein comprising seven myc epitope tags in the first extracellular domain and GFP or BFP in an intracellular domain, such as at the carboxy terminus. One example of DNA that encodes modified GLUT4 is represented in FIGS. 8A–8B (SEQ ID NO.: 8). Also included in this invention are variations of the DNA sequence of SEQ ID NO.: 8 that, due to the degeneracy of the genetic code, encode modified GLUT4, including the modified GLUT4 encoded by the DNA of SEQ ID NO.: 8 and proteins with sufficient similarity in sequence to that modified GLUT4 that they exhibit similar translocation characteristics (move to and from the cell membrane). DNA that hybridizes to the complement of DNA of SEQ ID NO.: 8 under high stringency conditions and encodes a protein with modified GLUT4 activity is also the subject of this invention, as is DNA that is at least 80% identical and preferably 90% and even more preferably 95 to 99% identical to DNA of SEQ ID NO.:8.

Modified GLUT4 is expressed in cells from a vector comprising GLUT4-encoding DNA and additional components sufficient to result in GLUT4 expression in the host cells used or is stably incorporated into host cell DNA and expressed therefrom.

A wide variety of vectors, particularly viral or retroviral vectors, are useful to produce modified GLUT4. Any retroviral vector which is of appropriate host range or can be modified to have an appropriate host range (e.g., capable of infecting the host cell type, e.g., mammalian, such as mouse, human, avian, reptilian, et al., used) is useful to produce modified GLUT4. In one embodiment, the pMX vector is used (Onishi, *Exp Hematol.* 24:324–329 (1996)). Alternatively, cells can be modified to make them susceptible to infection by a retrovirus of host range which does not infect the corresponding unmodified cells. For example, hamster cells, such as CHO cells, can be modified to render them injectable by a mouse retrovirus (which does not infect the corresponding unmodified hamster (e.g., CHO) cells). The present method of detecting and/or quantifying changes in the proportion of GLUT4 at the plasma membrane is carried out as follows: Cells (e.g., eukaryotic, such as, mammalian, including but not limited to, human, pig, rat, mouse, avian, reptilian) which express modified GLUT4 protein are cultured under (treated with) a condition (e.g., in the presence of insulin and/or a drug or agent to be assessed for its effects on translocation) which causes or enhances translocation to the cell membrane. These cells are referred to as test cells. Intensity of the intracellular label (e.g., intensity of fluorescence due to the intracellular tag) and of the extracellular (cell surface or plasma membrane) epitope tag (e.g., intensity of fluorescence due to the extracellular epitope tag) are determined. The intracellular label is indicative of total modified GLUT4 in the cells and the epitope tag is indicative of the amount of modified GLUT4 at the cell membrane (extracellular GLUT4). The proportion of cell membrane GLUT4 to total GLUT4 is calculated, to produce a test value or proportion. It is compared with a control value or proportion, which is the proportion of cell membrane GLUT4 to total GLUT4 calculated for control cells, which are the same as the test cells and are cultured under the same conditions (treated the same) as the test cells except in the absence of the condition or factor (e.g., in the absence of insulin) which is being tested to see if it causes or enhances a translocation to the cell membrane. If the proportion of cell membrane GLUT4 to total GLUT4 (test value) is greater for test cells than the corresponding proportion (control value) for control cells, a greater proportion of total GLUT4 is at the plasma membrane in the test cells than in the control cells and the condition(s) to which the cells were exposed enhances translocation. Conversely if the proportion is less for test cells than it is for control cells, the proportion of total GLUT4 at the cell membrane is less in the test cells than in the control cells and the condition(s) under which the cells were cultured inhibits translocation to the plasma membrane. Preferably, three sets of values, each consisting of fluorescence intensities at two distinct wavelengths, are determined in the method of assessing change in the proportion of a protein of interest, such as GLUT4, that is present at the plasma membrane (and, thus, the extent to which translocation has occurred). The following example makes specific reference to GLUT4, but the same procedures, calculations and analyses can be applied to any protein of interest whose translocation is to be assessed. The two wavelengths, F1 and F2, correspond, respectively, to cell surface (plasma membrane) GLUT4 and total GLUT4 reporter protein in the cell. Cell surface GLUT4 can be measured by a fluorophore (e.g., PE) coupled to an antibody that binds to externalized myc epitope tag, but not to intracellular myc epitope tag or by a secondary fluorophore-bearing antibody which recognizes a primary antibody that recognizes the myc epitope. The three sets of values are as follows:

1. background fluorescences of the cells used. Here, F1 (represented by A in the formula below) can be the fluorescence of cells expressing the modified GLUT4 protein but not stained with an antibody that recognizes the extracellular epitope tag or the fluorescence of cells that do not express the modified GLUT4 protein and are either unstained or stained with antibody that recognizes the extracellular epitope tag. In either case, there will be no fluorescence due to staining of extracellular epitope tag. F2 (represented in the formula by B) is the fluorescence of control cells that do not express modified GLUT4, which means that fluorescence detected at the wavelength of the intracellular tag (e.g., at the wavelength of GFP or BFP) is due only to intrinsic fluorescence of the cells and not to any GFP or BFP present;
2. fluorescence intensities (F1 and F2, represented, respectively, in the formula by C and D) of unstimulated cells (cells cultured in the absence of/not exposed to conditions to be assessed for their effects on translocation) which express the reporter protein and are stained with an antibody that recognizes the extracellular epitope tag is the total fluorescence due to staining of externalized epitope tag and background at that wavelength and D is the sum of fluorescence due to the intracellular tag and background at that wavelength; and
3. fluorescence intensities (F1 and F2, represented, respectively, in the formula by E and F) of stimulated cells (cells cultured in the presence of/exposed to conditions which cause or enhance translocation).

The following then applies:

(C−A)/(D−B) is proportional to the fraction of GLUT4 at the cell surface in unstimulated cells; (E−A)/(F−B) is proportional to the fraction of GLUT4 at the cell surface in stimulated cells; ((E−A)/(F−B))/((C−A)/(D−B))=G, which is the fold increase (or decrease) in the proportion of GLUT4 at the cell surface after stimulation (e.g., after insulin stimulation).

In some instances, the conditions to which the test cells are exposed may alter the background fluorescences of the test cells used. In this case, two sets of background fluorescences may be required. If A and B are background fluorescences for the control cells and A' and B' are background fluorescences for the test cells, then (C−A)/(D−B) is proportional to the fraction of GLUT4 at the cell surface in unstimulated cells, and (E−A')/(F−B') is proportional to the fraction of GLUT4 at the cell surface in stimulated cells and ((E−A')/(F−B'))/((C−A)/D−B))=G is the fold increase (or decrease) in the fraction of GLUT4 at the cell surface caused by the test conditions.

If G=1, then the condition to which the test cells (also referred to as stimulated cells) were subjected (e.g., stimulation by insulin) caused no change in the proportion of total GLUT4 at the cell surface. If G=5, then the condition (e.g., stimulation by insulin) caused a 5-fold increase in the fraction of total GLUT4 present at the cell surface. The proportion of total GLUT4 that is present at the cell surface.

This embodiment of the present method of determining or assessing translocation of GLUT4 from an intracellular location to the plasma membrane comprises:

(a) culturing cells expressing modified GLUT4 under conditions to be assessed for their effects on translocation of GLUT4, wherein modified GLUT4 is GLUT4 protein comprising at least one epitope tag in an extracellular domain and a fluorescent tag in an intracellular domain thereof and wherein the cells are referred to as test cells;

(b) determining the proportion of modified GLUT4 at the cell membrane to total modified GLUT4 in the test cells, thereby producing a test value;

(c) comparing the test value with a control value, wherein the control value is the proportion of modified GLUT4 at the cell membrane to total modified GLUT4 in control cells, wherein the control cells are the same cells as are cultured in (a) and are cultured under the same conditions as in (a), except that the control cells are not cultured under the condition or stimulus to be assessed. If the test value is greater than the control value, then there is a greater proportion of GLUT4 at the cell membrane of the test cells than at the cell membrane of control cells.

In particular embodiments, modified GLUT4 at the cell membrane is assessed (quantified or detected) by means of an antibody which is fluorescently labeled with a fluorophorie detectable at a wavelength different from the wavelength at which the fluorescent tag in the intracellular domain is detected and which binds the epitope tag at the plasma membrane (binds the extracellular epitope tag). Alternatively, modified GLUT4 at the cell membrane is assessed by means of a secondary antibody which bears a fluorescent label (an antibody that binds an antibody that recognizes the extracellular epitope).

As discussed above, in one embodiment, the test cells are assessed and the change in the proportion of GLUT4 at the cell surface is determined as follows: The fluorescence intensity at the cell surface (F1) is determined, as described herein (e.g., by use of a fluorescently labeled secondary antibody), thus providing a measure of GLUT4 at the cell surface of test cells. This value is designated (in the formula) E. The fluorescence intensity of the reporter protein (such as GFP or BFP, F2) is determined, thus providing a measure of total GLUT4 in test cells. This value is designated F in the formula. The fluorescence intensity at the cell surface and the fluorescence intensity of the reporter protein are determined for two types of control (or reference) cells, referred to as background control cells and unstimulated control cells, respectively, thus providing a measure of GLUT4 at the cell surface and a measure of total GLUT4 for both types of cells.

Background cells are the same type of cells as the test cells and are cultured under the same conditions as the conditions under which test cells are cultured, except that they are not subjected to the conditions to which the test cells are subjected in order to alter translocation of GLUT4. (For convenience, cells that are not subjected to the conditions or stimuli to which test cells are subjected in order to alter translocation of GLUT4 are referred to as "unstimulated cells"). Background cells are the same type of cells, but do not express the reporter protein, and therefore, any fluorescence detectable at the wavelength at which the reporter protein is detected results from intrinsic fluorescence of the background cells. In the formula presented above, F1 and F2 are represented, respectively by A and B, as described. As noted above, background may be measured using background cells that are subjected or not subjected to the stimuli, and may then be designated A and B (unstimulated) and A' and B' (stimulated).

Unstimulated control cells are also the same type of cells as the test cells and, like the test cells, express modified GLUT4. Unlike the test cells, unstimulated cells are not subjected to conditions to alter translocation. For example, if test cells are treated with insulin, in order to enhance translocation of GLUT4, unstimulated control cells are cultured under the same conditions except in the absence of insulin. Fluorescence intensity at the surface of unstimulated control cells (F1) is assessed, as described herein (e.g., by means of an antibody bearing a fluorophore), thus providing a measure of GLUT4 at the cell surface. The fluorescence intensity of the reporter protein (F2) is also determined, thus providing a measure of total GLUT4 in the unstimulated control cells. The intensity of F1 is designated C and the intensity of F2 is designated D for unstimulated control cells. Since short term (<30 min) insulin treatment does not alter background fluorescence, only one set of A and B is required in this example. The change in the proportion of GLUT4 at the cell surface of test cells (G) is assessed/calculated as follows in this embodiment: $G=[(E-A)/(F-B)]/[(C-A)/(D-B)]$ where $(E-A)/(F-B)$ is proportional to the fraction of GLUT4 at the cell surface in test cells and $(C-A)/(D-B)$ is proportional to the fraction of GLUT4 at the cell surface of unstimulated control cells. If G=1, the condition to which test cells were subjected (e.g., insulin stimulation, low glucose concentration, high glucose concentration) caused no change in the proportion of GLUT4 at the cell surface. If G is greater than 1, the condition to which test cells were subjected caused a change in the proportion of GLUT4 at the cell surface. For example, if G=5, the condition caused a 5-fold increase in the fraction of total GLUT4 at the cell surface.

The test cell values (fluorescence at the cell membrane and fluorescence of the intracellular tag or reporter protein) can be compared with control cell values (e.g., background control cell values and/or unstimulated control cell values) which are obtained through assessments carried out at the same time that test cells are assessed or obtained through assessments carried out prior or subsequent to assessment of test cells. In the latter instances, respectively, the test values are compared with a previously-established set of control values (a previously-established reference) or a subsequently-established set of control values (a subsequently-established reference).

The present invention also relates to a method of identifying a drug or agent that alters GLUT4 translocation from an intracellular location to the cell (plasma) membrane. In the method, cells in which modified GLUT4 is expressed (test cells) are combined with a candidate drug (a drug to be assessed for its ability to alter GLUT4 translocation) and the proportion of modified GLUT4 at the plasma membrane (relative to total GLUT4 in the cells) is determined and compared with the proportion of modified GLUT4 at the plasma membrane in control cells, which are cells of the same type as the test cells cultured under the same conditions as the test cells, but in the absence of the candidate drug.

In one embodiment of the present method by which a drug that enhances GLUT4 translocation to the cell membrane is identified, cells that express modified GLUT4 protein are cultured in the absence or presence of a candidate drug, for sufficient time for the effect (if any) of the candidate drug to be assessed. A candidate drug is one (a compound or molecule) whose effects are being assessed. In each case, the effect of insulin to cause an increase in the proportion of modified GLUT4 at the plasma membrane (relative to the total GLUT4 content of the cells) is determined and compared with the proportion of modified GLUT4 at the plasma membrane in an appropriate control or controls. For example, mammalian cells (which can be differentiated or undifferentiated) expressing modified GLUT4 protein are cultured with or without a candidate drug, as well as with or without conditions that stimulate GLUT4 translocation (e.g., the presence of insulin) and changes in the proportion of plasma membrane GLUT4 to total cell GLUT4 are determined for each set of conditions. Cells cultured in the presence of the drug are referred to as test cells and the resulting proportion of GLUT4 at the cell surface in the absence or presence of insulin (or other stimulator) is referred to as test values. The proportions of GLUT4 at the cell membrane in the test cells are compared with the proportions in control cells, which are cells of the same type as the test cells that are cultured in the same manner as are the test cells, except in the absence of the candidate drug. The proportion of GLUT4 at the cell surface in the presence or absence of insulin in the absence of the drug are referred to as control values. If the test values are greater than the control values, the candidate drug is a drug that enhances GLUT4 translocation to the cell membrane. In certain cases, the method measures actual proportions, while in other cases relative proportions are measured. An insulin sensitizing drug may enhance the ability of insulin to cause GLUT4 translocation to the cell surface.

In the present method of identifying a drug or agent that enhances or inhibits GLUT4 translocation to the cell membrane, an appropriate population of cells (such as adipocytes, an adipocyte cell line, muscle cells, a muscle cell line or any other cell type in which GLUT4 exocytosis is stimulated by insulin) in which modified GLUT4 is expressed (referred to as test cells) is combined with a drug to be assessed for its effects on GLUT4 translocation. Modified GLUT4 is expressed from a vector present in the test cells or is stably incorporated into the host cell DNA and expressed. Prior to stimulating cells for GLUT4 translocation, cells can be preconditioned by subjecting them to conditions which mimic insulin resistance. The resulting combination is maintained under appropriate conditions and for sufficient time for the drug to have its effect on the cells, which are referred to as treated cells. The treated cells are exposed to or contacted with a substance, such as insulin, which induces GLUT4 translocation. This results in stimulation of GLUT4 translocation in the treated cells. GLUT4 translocation is assessed by determining the extent to which the epitope tag occurs extracellularly, normalized to the total amount of the GLUT4 reporter present, as described above. This is done using known methods, such as by an immunoassay or by measuring fluorescence at the membrane. If there is greater proportion of total GLUT4 at the plasma membrane in test cells than in untreated cells (such as cells of the same type as the test cells which have not been treated with the drug but are otherwise maintained under the same conditions), the drug or agent is one which enhances GLUT4 translocation.

In one embodiment of the method to determine whether a drug enhances GLUT4 translocation, eight types of cells can be assessed: 1) cells which express modified GLUT4 and are stimulated by insulin or subjected to conditions which mimic insulin resistance; 2) cells which express modified GLUT4 and are not stimulated by insulin or subjected to conditions which mimic insulin resistance; 3) cells which do not express modified GLUT4 and are stimulated by insulin or subjected to conditions which mimic insulin resistance; 4) cells which do not express modified GLUT4 and are not stimulated by insulin or subjected to conditions which mimic insulin resistance and; 5)–8) cells treated the same as cells in 1)–4), but in the presence of the drug. Cells which do not express modified GLUT4 are an additional control, in that they indicate the background fluorescence. The cells will express varying amounts of the construct and this can be monitored by assessing fluorescence using GFP or another fluorescent tag. No change in green fluorescence in the cell population indicates that the treatment has not caused an increase in extracellular myc tag levels by affecting the amount of the protein present, since if the treatment increased the amount of the protein present, there would also be an increase in green fluorescence due to the myc tag (e.g., red fluorescence) to green fluorescence indicates where the modified GLUT4 is located in the cell (inside the cell or extracellularly).

The present invention is illustrated by the following examples, which are not intended to be limiting in any way.

EXAMPLE 1

GLUT4 Translocation Assay

A GLUT4 translocation assay was carried out as follows: 3T3 L1 preadipocytes were infected with a retrovirus encoding a GLUT4 construct fused to green fluorescent protein (GFP) at its carboxy terminus, and containing seven myc epitope tags in the first exofacial loop. A population of cells expressing a narrow window of green fluorescence was isolated by fluorescence activated cell sorting (FACS). These cells were propagated and differentiated on 10 cm plates, and were reseeded on 6-well dishes the day prior to performing the GLUT4 translocation assay. Cells were serum starved for 3 hours, then stimulated or not with 160 nM insulin for 10 minutes. They were then placed on ice and washed with cold phosphate buffered saline with calcium and magnesium (PBS++). All subsequent steps were done at 4° C. Cells were incubated with anti-myc antibody (9E10), washed briefly with PBS++, and incubated with phycoerythrin-conjugated F(ab)2 antimouse IgG. Cells were washed with PBS++, resuspended using EDTA, and analysed by two color flow cytometry.

Use of a retroviral vector to express the DNA construct makes it possible to work with a pool of cells, instead of a single clone. In addition, 3T3L1 cells are propagated as fibroblasts and can be induced to differentiate into fat cells only if they are maintained at a subconfluent density. This condition is met if retroviral infection of a population of cells is used, rather than transection and clonal selection.

One protocol for carrying out the method of assessing translocation of modified GLUT4 is as follows: 3T3L1 cells are maintained at a subconfluent density, infected with retrovirus expression vectors which include DNA encoding modified GLUT4 and induced to differentiate into adipocytes. After being cultured (e.g., for 8–12 days) under appropriate conditions, the cells are reseeded onto plates (e.g., 6-well plates) and serum starved (e.g., for 3 or more hours). Some cells are stimulated by insulin (e.g., 160 nM, 10 minutes), placed on ice and washed at 4° C. with PBS++(phosphate buffered saline containing calcium and magnesium). Anti-myc antibody (9E10, available from the American Type Culture Collection) is added to the cells (40 g/ml, 11/2 hours, 4° C.). The cells are again washed with PBS++ at 4° C. and an antimyc antibody labeled with a red fluorophore (R-phycoerythrin (R-PE) conjugated antimouse IgG, 50 $\mu$g/ml, 45 minutes, 4° C.) is added. Another washing with PBS++(4° C.) is carried out, the cells are suspended with EDTA and FACS (fluorescences activated cell scanning/sorting) is carried out.

A FACS-based assay has several advantages. For example, because gating is possible, adipocytes can be assessed without interference from fibroblasts. In addition, a FACS-based assay is quantitative; it can be carried out on a cell by cell basis and the geometric mean or median can be used (as opposed to the arithmetic mean obtained when a plate reader is used; the mean can be skewed by a few bright cells). Further, FACS-based assessment is rapid (e.g., 1000 events can be assessed/second in the gated region) and flexible (e.g., 5–7 parameters can be viewed simultaneously for each cell). Sorting is also possible and permits enrichment. It should be noted that GFP, BFP or other fluorescent marker can also be used to sort cells, to produce a substantially pure population of cells, at any level of expression.

The following materials and methods were used in the following examples.

Antibodies and Reagents

Cell culture media and supplements were purchased from Life Technologies (Grand Island, N.Y.) and JRH Biosciences (Lenexa, Kans.). Anti-c-myc monoclonal antibody (clone 9E10) was from Babco (Richmond, Calif.). Normal Donkey serum and R-phycoeiythrin conjugated donkey $F(ab')_2$ anti-mouse IgG secondary antibody were purchased from Jackson Immunoresearch (West Grove, Pa.). Restriction enzymes were from New England Biolabs (Beverly, Mass.) and Pfu and Taq DNA polymerases were from Stratagene (La Jolla, Calif.). Wortmannin and LY294002 were from Calbiochem (La Jolla, Calif.). Oil Red O and other chemicals were from Sigma (St. Louis, Mo.).

Cell Culture

Murine 3T3-L1 fibroblasts were cultured in Dulbecco's modified Eagle's medium (DMEM) containing 10% fetal bovine serum and differentiation was induced according to established protocol (Frost, S. C. and Lane, M. D., *J Biol Chem.,* 260:2646–2652 (1985); Bogan, J. S. and Lodish, H. F., *J Cell Biol.* (1999)). Briefly, cells were allowed to reach confluence at least two days prior to the induction of differentiation. Differentiation was induced (on "Day 0") with medium containing 0.25 M dexamethasone, 160 nM insulin, and 500 M methylisobutylxanthine. After 48 hours ("Day 2"), the cells were fed with medium containing 160 nM insulin. After an additional 48 hours ("Day 4"), the cells were refed every two days with DMEM/10% fetal bovine serum. All media were supplemented with 2 mM glutamine, 100 U/ml penicillin, and 0.1 mg/ml streptomycin. Differentiation was monitored by noting the accumulation of lipid droplets, which typically began by Day 4 of differentiation. Cells were considered fully differentiated between Days 8 and 12. The terms "Day 0 3T3-L1 cells" and "confluent 3T3-L1 fibroblasts" are used interchangeably herein.

CHO-K1 cells stably expressing the murine ecotropic retroviral receptor were kindly provided by David Hirsch, Roger Lawrence, and Monty Kreiger (Massachusetts Institute of Technology, Cambridge Mass.), and were maintained in Han's F-12 medium with 10% fetal bovine serum, 2 mM glutamine, 100 U/ml penicillin, and 0.1 mg/ml streptomycin (Baker, B. W., et al., (1992)). To use identical experimental conditions in CHO and 3T3-L1 cells, CHO cells were placed in the same medium used for 3T3-L1 adipocytes two days before assays of GLUT4 trafficking. Phoenix ecotropic retroviral packaging cells were a gift from Garry Nolan (Stanford University Medical Center) and VE23 ecotropic retroviral packaging cells were a gift from Merav Socolovsky (Whitehead Institute, Cambridge Mass.) (Kinsella, and Nolan, *Hum Gene Ther.* 7:1405–1413 (1996); Socolovsky, M., et al. *J Biol Chem.* 272:14009–14012 (1997)). Both retroviral packaging cell lines were cultured in DMEM, 10% fetal bovine serum, glutamine, penicillin and streptomycin as above.

Construction of a GLUT4 reporter

A human GLUT4 cDNA containing a c-myc epitope tag in the first exofacial loop was kindly provided by Zhijun Luo and Joseph Avruch (Massachusetts General Hospital, Boston Mass.). This clone had been constructed as described by Kanai, F. et al., *J Biol Chem.* 268:14523–14526 (1993)). We fused the GFP coding sequence in frame to the carboxy terminus of this GLUT4 clone based on the result of Dobson et al. (1996), that GLUT4-GFP appears to localize and traffic similarly to wildtype GLUT4. The GFP coding sequence from pEGFP-N1 (Stratagene) was first cloned into the pMX retroviral vector using EcoRI and NotI, to generate the plasmid pMX-GFP (Onishi, M., et al. *Exp Hematol* 24:324–329 (1996)). PCR was done using the primers 5'-GACATTTGACCAGATCTCGG-3'(SEQ ID NO.: 2) and 5'-GGCCCGCGGGTCATTCTCATCTGGCCC-3'(SEQ ID NO.: 3) to generate an approximately 110 bp Bg1II/SacII fragment from the 3' end of the rat GLUT4 cDNA (Charron, M. J., et al., *Proc Natl Acad Sci USA*. 86:2535–2539 (1989)). This PCR product and an EcoRI/Bg1II fragment containing most of the GLUT4myc cDNA were used in a three-way ligation with EcoRI/SacII-digested pMX-GFP, to generate pMX-GLUT4myc-GFP. Next, six additional myc epitope tags were added in tandem with the existing myc epitope tag, for a total of seven myc epitope tags. PCR was first used to amplify approximately 240 bp EcoRI/HindIII fragment including the 5' end of the rat GLUT4 cDNA and part of a myc tag, using the primers 5'-CCGGCCGAATTCATGCCGTCGGGTTTCCAG CAGATC-3' (SEQ ID NO.: 4) and 5'-CTTCAGAAATAAQCTTTTOCTCCTCTOCAG GACCCTGCCTACCCAGCCAAGT TGC-3' (SEQ ID NO.: 5). This fragment was used to replace a corresponding fragment in pMX-GLUT4myc-GFP, creating a unique HindIII site within the myc epitope tag. A HindIII fragment containing six tandem myc epitope tags was amplified from the plasmid pCS2+MT, a gift of Bill Schiemann (Whitehead Institute, Cambridge Mass.), using the primers 5'-CCATCGATTTAAAGCTATGGAGCAAAAGCTT ATTTCTGAAGAGG-3' (SEQ ID NO.:6) and 5' CAGAAATAAGCTTTTGCTCCTCTGCAG-GCTCAAGAGGTCTTGAGTTCAAGTC CTCTTC-3' (SEQ ID NO.: 7). This fragment was inserted into the HindIII site of pMX-GLUT4myc-GFP, creating pMX-GLUT4myc7-GFP. The entire coding regions of the pMX-GLUT4myc-GFP and pMX-GLUT4myc7-GFP plasmids were verified by sequencing. Cells infected with pMX-GLUT4myc-GFP were used for the experiments presented in all other experiments presented employed cells infected with pMX-GLUT4myc7-GFP.

Production of Retroviral Supernatant and Isolation of Infected Cell Populations

Phoenix or VE23 ecotropic packaging cells were transfected with pMX-GLUT4myc-GFP or pMX-GLUT4myc7-GFP plasmids using calcium phosphate as described (Kinsella, T. M. and Nolan, G. P., Human Gene Ther., 7:1405–1413, (1996)). Media containing recombinant retroviruses were harvested 48 or 72 hours after transfection, and were used to infect dividing 3T3-L1 fibroblasts or CHO cells expressing the murine ecotropic receptor. For 3T3-L1 fibroblasts infected with pMX-GLUT4myc7-GFP, flow cytometry demonstrated the presence of GFP in >90% of cells after infection. Stable populations of infected cells expressing 'high', 'medium', or 'low' amounts of the reporter were isolated by flow sorting cells falling within narrow windows of GFP fluorescence. The sorted cells were expanded, and insulin-stimulated GLUT4 trafficking was measured in all cases. T he fold translocation (stimulated/basal) was greatest in the cells expressing a 'medium' amount of the reporter, and these cells were used in all subsequent experiments. It is possible that the trafficking mechanism may have been saturated in the cells expressing a 'high' amount of reporter, and the signal/noise ratio was suboptimal in the cells expressing a 'low' amount. Similar optimization of reporter expression levels was carried out in CHO cells.

Measurement of Plasma Membrane GLUT4 Trafficking By Flow Cytometry

Confluent cells were reseeded on the indicated day of differentiation to six well plates (Corning, Costar #3506) one day before use in experiments, and were starved in DMEM without fetal bovine serum for at least 3 hours before insulin stimulation. Insulin was used at 80 nM or 160 nM; no difference was noted between these concentrations in either 3T3-L1 or CHO cells. After treatment in the presence or absence of insulin for the times indicated in each figure, cells were quickly transferred to 4° C. and washed with cold phosphate buffered saline containing 0.9 mM $Ca^{++}$ and 0.5 mM $Mg^{++}$ (PBS++). All subsequent steps were carried out at 4° C., and staining of externalized myc epitope was done on adherent cells. Cells were incubated with a 1:200 dilution of anti-myc (9E 10) ascites in PBS++, 2% bovine serum albumin, 4% donkey serum for 1.5 hours. Cells were then washed twice in PBS++, for 5 min. each time. They were then incubated 45 min. in 12.5 g/ml R-phycoerythrin conjugated donkey $F(ab')_2$ anti-mouse IgG secondary antibody, diluted in PBS++, 2% BSA, 4% donkey serum. Cells were washed three times with PBS++, for 10 min. each time, and were resuspended by gentle scraping in PBS++, 2% BSA for flow cytometry. For experiments involving insulin removal, cells were chilled as above after insulin stimulation, then washed twice with 5 mM sodium acetate, 150 mM NaCl, pH 4.0 (Yang, J., et al., *J Biol Chem.* 267:1039310399 (1992); Kao, A. W., et al., *J Biol Chem.* 273:25450–25457 (1998)). Cells were rewarmed in 37° C. DMEM for the times indicated, restimulated or not with insulin, and then returned to 4° C. and chilled with cold PBS++ before staining as above.

Flow cytometry was done on FACScan or FACSCalibur cytometers (Becton-Dickinson). Appropriate compensation between the FL1 and FL2 channels was set using uninfected (GFP-negative) cells or cells stained with PE only (e.g. using a PE-conjugated anti-transferrin receptor antibody, Pharmingen). Pilot experiments demonstrated minimal loss of viability; only 2% to 3% of the cells typically stained with propidium iodide using the protocol described above, so propidium iodide was not used in experiments where accurate compensation and quantitation of fluorescence intensities was essential. For each sample, data from ≧10,000 cells were collected. Median fluorescence intensities were used for quantitation, since this measure of central tendency is least sensitive to outliers. For each sample, the PE and GFP fluorescence specifically attributable to the presence of the GLUT4 reporter were determined by subtracting background fluorescences, measured using control unstained cells and cells not expressing the reporter, respectively.

Other methods

Time lapse video fluorescence microscopy was performed using a Nikon Diaphot 300 inverted microscope as described (Smith, G. A., et al., *J Cell Biol.* 135:647–660 (1996)). 3T3-L1 adipocytes expressing GLUT4myc-GFP were reseeded to 25 mm round coverslips and were incubated in serum-free DMEM for at least three hours before microscopy. Cells were maintained at 37° C. during microscopy using an aluminum chamber mounted on the stage and connected to a circulating waterbath. Images were acquired every 15 sec using a Hammamatsu CCD camera and Metamorph software (Universal Imaging Corp., West Chester Pa.).

Oil Red O staining was done on cells grown in 10 cm dishes. Cells were fixed with 4% paraformaldehyde for 45 min. at room temperature, permeablized with 0.2% Triton X-100 for 5 min. at 4° C., and stained using a 2 mg/ml solution of Oil Red O in ethanol (Green, H. and Kehinde, O., *Cell,* 5:19–27, (1975)). Phase contrast and brightfield microscopy was done using an Olympus inverted microscope.

EXAMPLE 2

A Novel Assay for GLUT4 Trafficking at the Plasma Membrane

A cDNA encoding a GLUT4 reporter protein was constructed to assay changes in the proportion of GLUT4 that is present at the plasma membrane. This protein contains seven c-myc epitope tags in the first exofacial loop of GLUT4, and GFP fused in-frame at the carboxy terminus. As shown in Fig. 1A, expression of this protein in cells enabled measurement of changes in the proportion of GLUT4 at the cell surface as changes in the ratio of fluorescence intensities corresponding to cell-surface and total amounts of the reporter. An anti-myc primary monoclonal antibody, followed by a phycoerythrin (PE)-conjugated secondary antibody, was used to detect reporter protein present at the surface of living cells. Green (GFP) fluorescence indicates the total amount of the reporter present in each cell. Thus, the ratio of PE to GFP fluorescence intensities corresponds to the proportion of total GLUT4 that is present at the plasma membrane. Flow cytometry was used to measure these fluorescence intensities simultaneously and on a cell-by-cell basis.

Figure 1B:
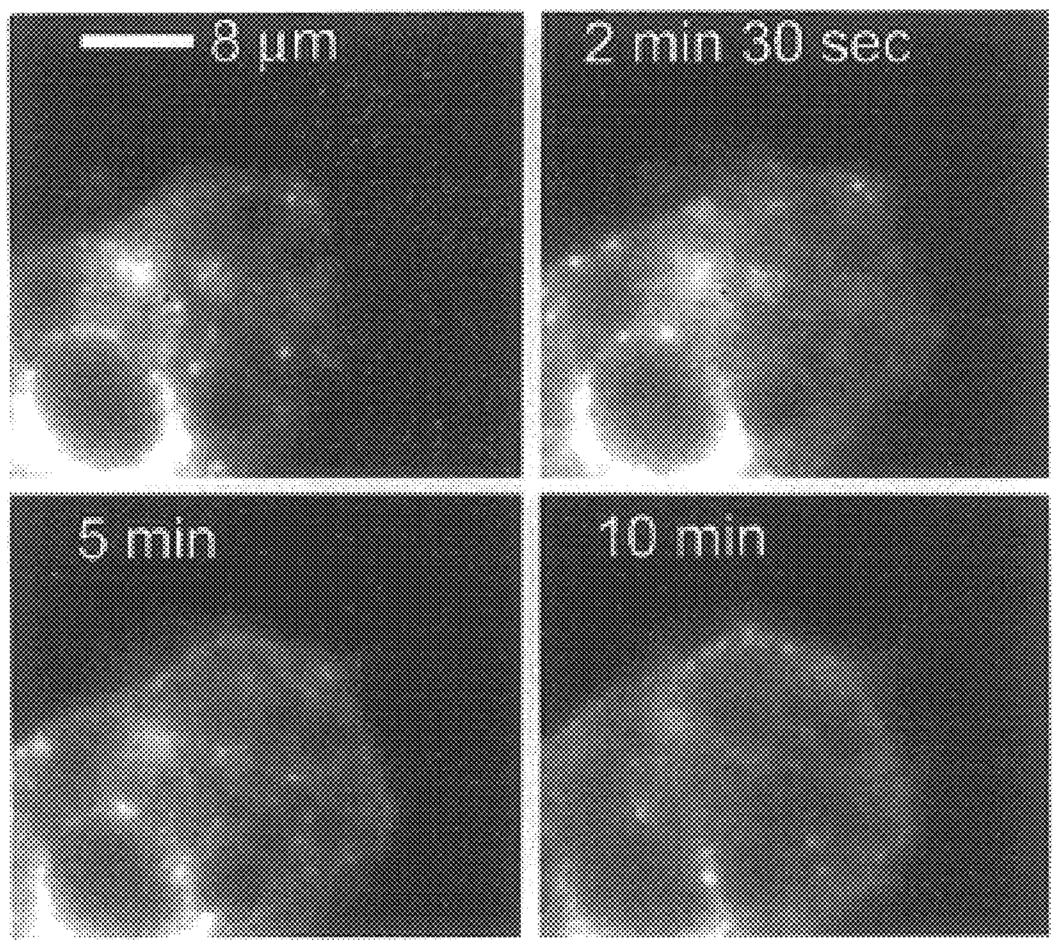

The GLUT4 reporter in a murine retroviral vector was used to infect 3T3-L1 fibroblasts. The infected cells underwent normal adipose differentiation (see below), and we took several approaches to confirm that the GLUT4 reporter traffics appropriately. FIG. 1B shows four frames from a time-lapse fluorescence microscopy video, detecting the GLUT4-myc-GFP fusion protein before and at various times after insulin addition (for this experiment the myc epitope tag was not used for detection). In the absence of insulin, GFP fluorescence is present in the perinuclear pattern that is characteristic of GLUT4, as well as in punctate structures near the plasma membrane and throughout the cytoplasm. Lipid droplets are present in the cytoplasm, and are seen as discrete areas of reduced fluorescence intensity. Insulin addition results in a redistribution of fluorescence to the plasma membrane; this is punctate at 2.5 minutes after insulin addition, but becomes more evenly dispersed along the membrane at 5 and 10 minutes after insulin stimulation.

Figure 1C:
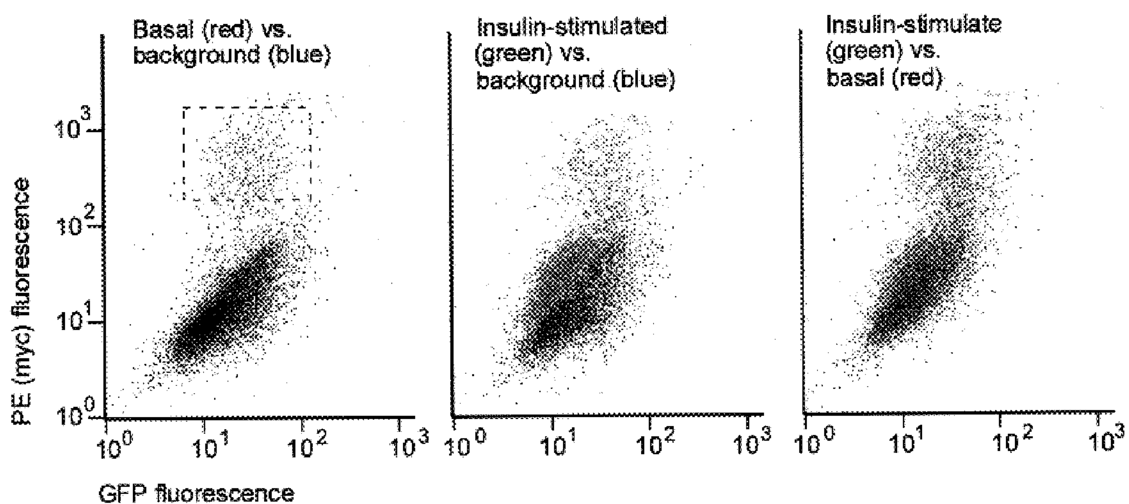

Fluorescence activated cell sorting (FACS) was used to isolate a population of 3T3-L1fibroblasts with a narrow range of GFP fluorescence intensities; individual cells in this population express similar amounts of the reporter protein. These 3T3-L1 cells were induced to undergo adipocyte differentiation, and insulin-stimulated GLUT4 exocytosis was measured as shown in FIG. 1C. FACS was used analysis to detect simultaneously PE fluorescence (corresponding to cell-surface GLUT4 reporter and shown on the vertical scale) and GFP fluorescence (corresponding to total GLUT4 reporter and shown on the horizontal scale). For unstained cells (shown in blue), fluorescence along the PE axis is due entirely to the background autofluorescence of the cells themselves. Control experiments using secondary antibody without primary (anti-myc) antibody, as well as control experiments using both primary and secondary antibodies on cells not expressing the reporter, demonstrate that background staining is negligible; thus, essentially all of the increase in PE fluorescence observed in the basal (red) and insulin-stimulated (green) populations is due to detection of myc on the cell surface. Similarly, the GFP fluorescence attributable to the GLUT4 reporter can be determined by subtracting the background autofluorescence, measured using uninfected cells. Within each population of stained cells (basal and insulin-stimulated), the amount of staining for cell-surface myc correlates with the amount of the reporter present and, therefore, with GFP fluorescence. The populations therefore lie along a diagonal, and GLUT4 exocytosis results in a net translocation of the entire population upwards, along the PE axis, with no change in the slope of the diagonal. No saturation of the recycling mechanism was observed within this defined population of cells; changes in the proportion of GLUT4 at the cell surface are equivalent, even among cells expressing varying amounts of the reporter.

EXAMPLE 3

Figure 2A:
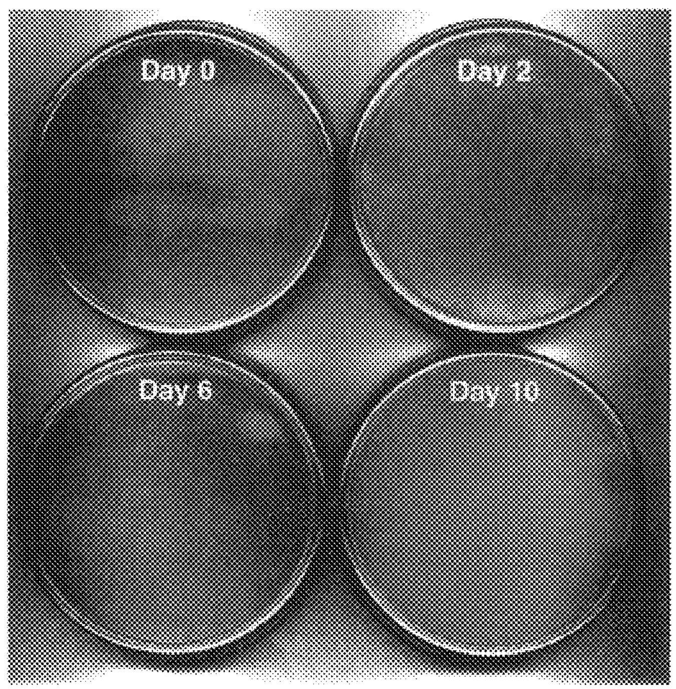
FIGS. 2A and 2B show results of assessment of adipose differentiation of 3T3-L1 cells expressing a GLUT4 reporter.
Figure 2B:
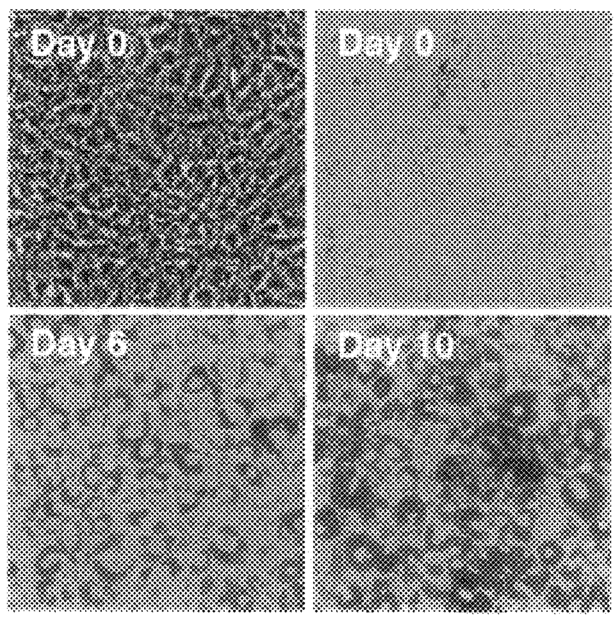

Insulin Stimulates GLUT4 Exocytosis Similarly in Undifferentiated 3T3-L1 Cells and Throughout 3T3-L1 Adipose Differentiation One difficulty in working with 3T3-L1 cells is that if the undifferentiated fibroblasts are allowed to become confluent, they must either be induced to undergo adipose differentiation or they will lose that capacity. This characteristic makes the introduction of exogenous proteins by stable transfection technically difficult, since the cells invariably become confluent during clonal selection. To circumvent this difficulty, a pool of cells infected with a replication-deficient retrovirus encoding the reporter protein was isolated. Over 90% of the target 3T3-L1 fibroblasts were infected, and those falling within a narrow window of GFP fluorescence were isolated by FACS. These cells were expanded and used in experiments; individual cells in this sorted population express similar amounts of the reporter. Because the retrovirus integrates into the genome, the population is stable. FIG. 2A (gross) and FIG. 2B (microscopic) demonstrate that these sorted cells undergo normal 3T3-L1adipose differentiation, as assessed by Oil red O staining to highlight the development of intracellular lipid droplets.

Figure 3A:
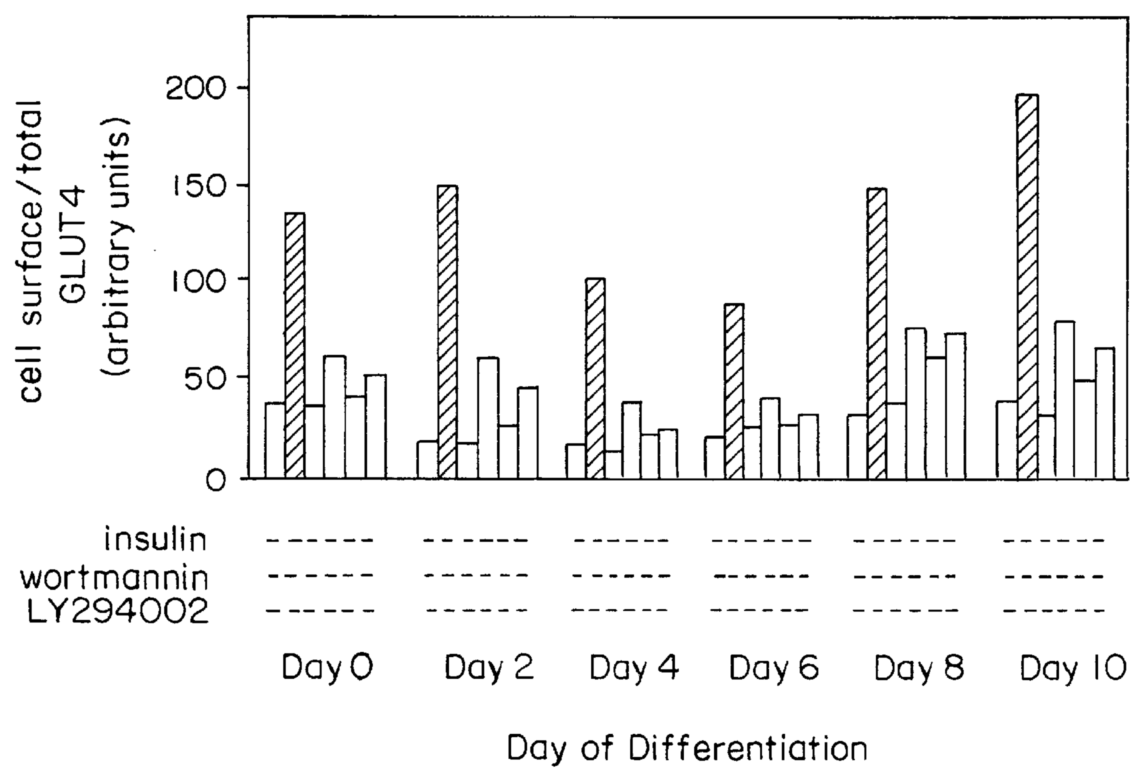
FIGS. 3A and 3B show results demonstrating that insulin triggers GLUT4 exocytosis at all times during differentiation of a 3T3-L1 cell line.

Determination of when, during the course of 3T3-L1 adipocyte differentiation, the cells become competent to translocate GLUT4 to the plasma membrane after insulin addition was made. Cells expressing the reporter were differentiated to different days, 20 and the ability of insulin to stimulate GLUT4 exocytosis was tested as described above. Surprisingly and as shown in FIG. 3A (and subsequently in FIGS. 4 and 5), results showed that insulin stimulates GLUT4 exocytosis at all stages of 3T3-L1differentiation, even in undifferentiated, confluent fibroblasts. Moreover, as shown in FIG. 3A, insulin-triggered GLUT4 exocytosis is invariably blocked by pretreatment of the cells with PI3K inhibitors, either 100 nM wortmannin or 50 M LY294002 for 40 minutes prior to insulin addition. Results of several experiments showed that we noted that the overall fold-increase in cell-surface GLUT4 is greater at Day 2 of differentiation than at Day 0, primarily due to more pronounced intracellular sequestration in unstimulated cells; nonetheless the effect at Day 0 is robust and dramatic (FIGS. 3A and 3B, and see below).

Figure 3B:
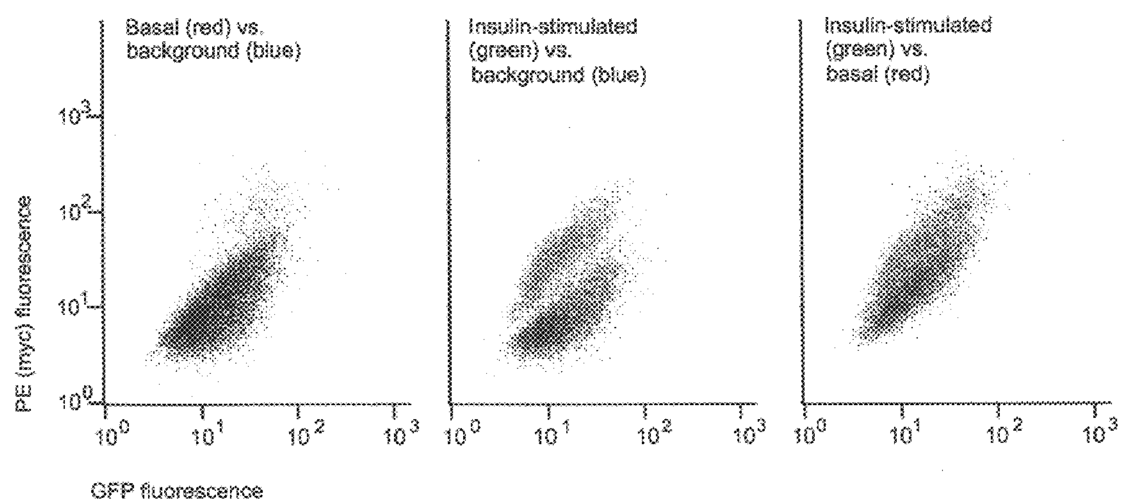

FIG. 3B shows the distribution of PE- and GFP-fluorescence intensities in confluent 3T3-L1fibroblasts. Comparison of these dot plots to those for 3T3-L1 adipocytes (FIG. 1C) demonstrates that the differences are minimal. In both cases there is substantial overlap of the background and basal populations (left panels). In both cases insulin stimulation results in increased staining for cell surface myc, so that there is little overlap of insulin-stimulated and background cells (center panels). In both cases, the basal and insulin stimulated populations fall along parallel diagonals (right panels), with translocation of the stimulated population upward on the PE axis. Perhaps the only substantive difference between the dotplots for 3T3-L1 fibroblasts and adipocytes is that the fibroblast plots are cleaner, with essentially no fragmented cells.

To determine if the kinetics of insulin-stimulated GLUT4 externalization vary during the course of 3T3-L1 differentiation, cells were stimulated on different days of differentiation and changes in the proportion of total GLUT4 at the cell surface were assayed after various amounts of time.

Confluent 3T3-L1 fibroblasts ('Day 0') or 3T3-L1 cells at various stages of adipocyte differentiation (as indicated) were treated with insulin for various lengths of time, and changes in the proportion of GLUT4 reporter present at the cell surface were analyzed. Data are plotted for basal cells and for cells treated with 80 nM insulin for 0.5, 1, 1.5, 2, 3, 4, 5, 6, 8, 10, 12, 15, 20, or 30 min. Membrane trafficking was stopped by washing with cold PBS, cells were stained at 4° C. for externalized myc epitope tag using a PE-conjugated secondary antibody, and PE and GFP fluorescence intensities were measured using flow cytometry as described in the text. Regardless of the state of differentiation, insulin causes a rapid externalization of GLUT4 which peaks 4 to 5 minutes after insulin addition. Subsequently there is a net internalization, such that a steady state in the presence of insulin is reached 20 minutes after insulin addition.

Figure 4:
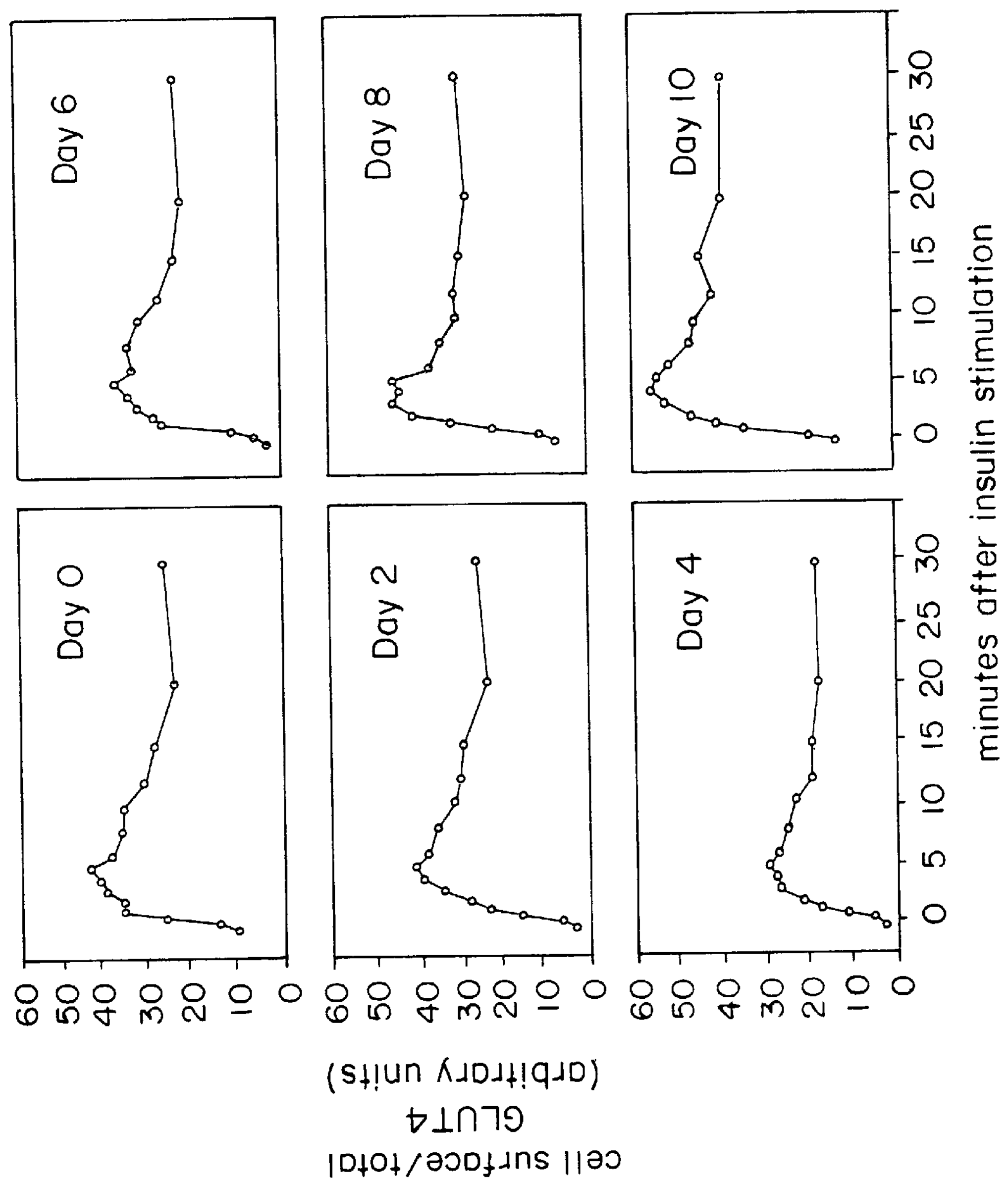
FIG. 4 is a series of graphs of results demonstrating that the kinetics of GLUT4 externalization after insulin stimulation are identical at all times during 3T3-L1 adipocyte differentiation.

As shown in FIG. 4, insulin triggers a rapid redistribution of GLUT4 to the cell surface, with identical kinetics at all stages of 3T3-L1 differentiation. In all cases there is a biphasic response to insulin addition, with an initial rapid externalization of GLUT4 such that the greatest proportion is present on the plasma membrane four to five minutes after insulin addition. Subsequently, in all cases, the fraction of GLUT4 on the plasma membrane falls by 30% to 40%, and reaches a steady-state by 20 minutes after insulin addition. Because of the relative ease with which it is possible to measure GLUT4 at the cell surface, all of the data points presented in all six panels of FIG. 4 were acquired in the same experiment. Additionally, as noted above, the assay is internally controlled for the amount of reporter present within each cell. Thus, any data point in any of the six panels can be directly compared to any other data point in the figure. Clearly, unstimulated Day 2 cells have a lower proportion of GLUT4 on the cell surface than unstimulated confluent fibroblasts (Day 0 cells), in agreement with the data presented in FIG. 3A. While the slightly higher basal level of GLUT4 at the surface of confluent fibroblasts lessens the overall "fold-increase" in cell surface GLUT4 after insulin addition, the overall picture is qualitatively similar in undifferentiated 3T3-L1 cells and in cells that have undergone any degree of adipose differentiation.

Figure 5:
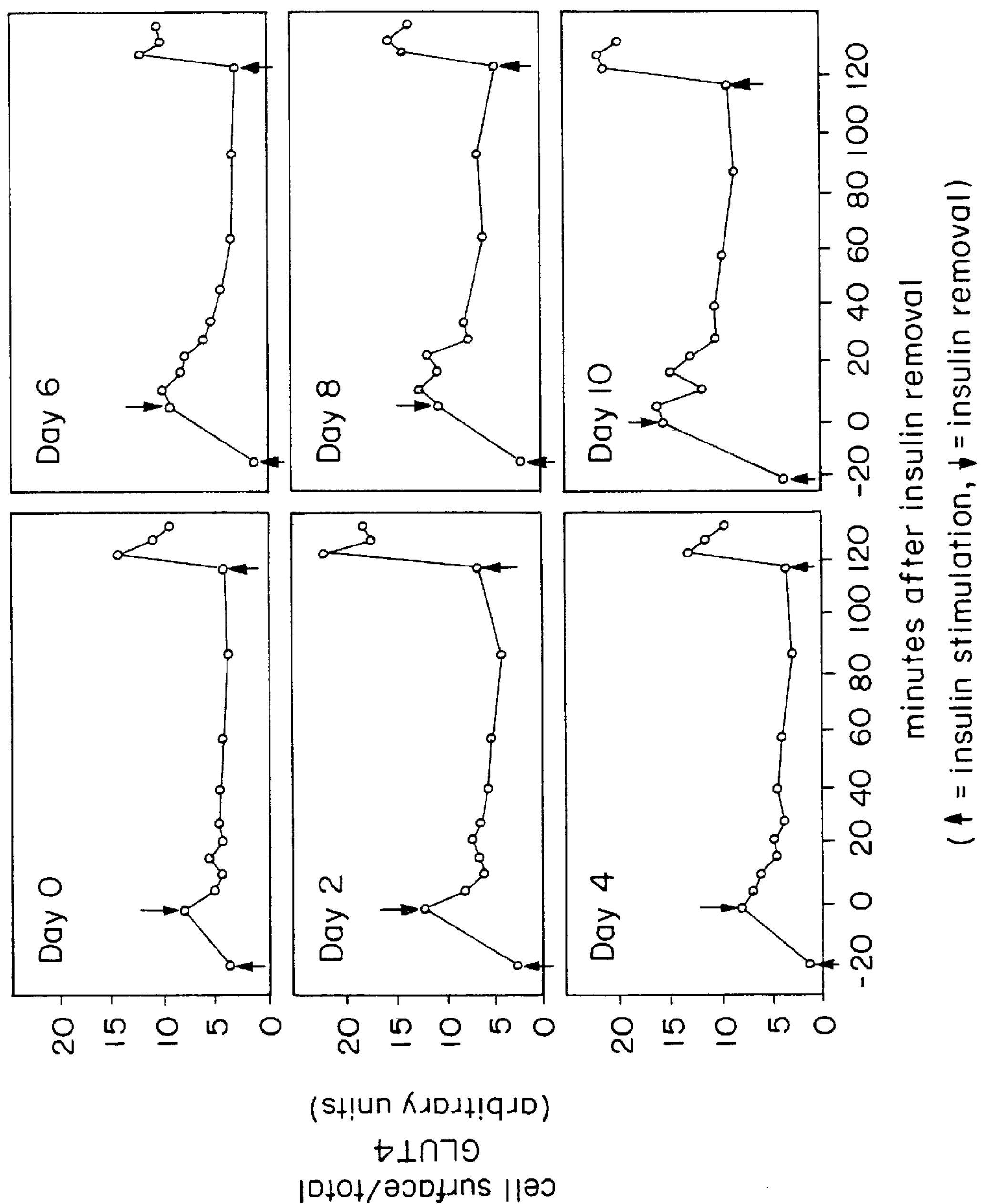
FIG. 5 is a series of graphs of results demonstrating that the GLUT4 reporter is reinternalized after insulin removal, and recycles upon insulin readdition, at all times during 3T3-L1 adipocyte differentiation. Confluent 3T3-L1 fibroblasts ('Day 0') or cells at various stages of adipocyte differentiation were stimulated with 80 nM insulin for 20 min., then placed at 4° C. and washed with an acidic buffer to remove insulin. Cells were rewarmed in serum free medium to allow GLUT4 reinternalization for 6, 12, 18, 24, 30, 40, 60, 90, or 120 min.; some cells that had been rewarmed for 120 min. were restimulated with 80 nM insulin for 5, 10, or 15 min. Cells were stained for cell surface myc epitope and analyzed by flow cytometry as described in the text. In all instances, the GLUT4 reporter is reinternalized after removal of insulin, and recycles upon readdition of insulin.

Reinternalization and recycling of the GLUT4 reporter after insulin removal was also examined. Based on the results shown in FIG. 4, cells were stimulated with insulin for 20 minutes so that the redistribution of GLUT4 to the plasma membrane would be at steady-state, then chilled, washed with a low pH buffer to remove insulin, and rewarmed in serum-free medium for varying amounts of time. Cells were allowed to reinternalize GLUT4 for up to two hours, at which time they were restimulated with insulin for 5, 10, or 15 minutes. As shown in FIG. 5, the reporter protein is reinternalized in undifferentiated 3T3-L1cells and at all stages of 3T3-L1 adipocyte differentiation, and is recycled upon restimulation with insulin in all cases. As in previous figures, all of the data points were collected in parallel and can be compared, even if presented in different panels of the figure. The rate of reinternalization is slightly prolonged in more differentiated cells as compared to less differentiated cells. Finally, restimulation with insulin causes reexternalization of the reporter, and the magnitude of this effect is similar to the initial response. The addition of myc epitope tags and fusion of GFP to the carboxy terminus of GLUT4 does not impair its ability to undergo endocytosis or insulin-stimulated recycling at the plasma membrane. Additionally, these data strengthen the primary result that insulin regulates GLUT4 recycling similarly in 3T3-L1 fibroblasts and adipocytes.

EXAMPLE 4

Insulin Stimulates GLUT4 Exocytosis in CHO Cells

Figure 6:
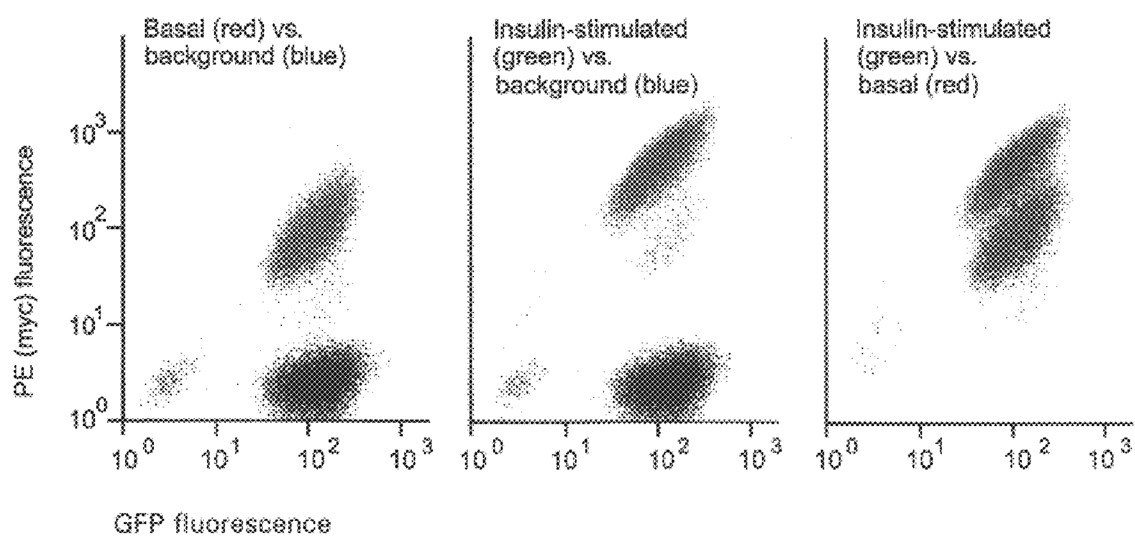
FIG. 6 presents results demonstrating that insulin stimulates GLUT4 exocytosis in CHO cells. Confluent CHO cells expressing the GLUT4 reporter were stimulated with 80 nM insulin for 8 min., then chilled, stained for externalized myc epitope, and analyzed by flow cytometry. As in FIGS. 1C and 3B, PE fluorescence (proportional to cell surface GLUT4 reporter) is plotted on the vertical axis and GFP fluorescence (proportional to total GLUT4 reporter) is plotted on the horizontal axis. Background (unstained) cells are shown in blue, basal and insulin-stimulated populations are shown in red and green, respectively. The three panels allow direct comparison between each pair of samples. There is a minor population of unstained cells (blue) within the first decade of each scale; these cells do not express the GLUT4 reporter and conveniently demonstrate that the flow cytometer is properly adjusted to compensate for fluorophore bleedthrough. In this experiment, insulin stimulated a 3.5-fold increase in the proportion of total GLUT4 present at the cell surface.

Thus, results demonstrated that insulin stimulates GLUT4 redistribution to the plasma membrane similarly in 3T3-L1 fibroblasts and at all times during 3T3-L1 adipocyte differentiation. Whether this recycling mechanism is present in an unrelated cell type was also assessed. This was done by infecting Chinese Hamster Ovary (CHO) cells expressing the murine ecotropic retroviral receptor with a retrovirus carrying the GLUT14 reporter, and using FACS to isolate cells falling within a narrow range of GFP fluorescence intensities. Externalization of the GLUT4 reporter was noted upon insulin stimulation of these cells, as shown in FIG. 6. CHO cells are smaller and have less autofluorescence than 3T3-L1 adipocytes or fibroblasts. The overall GFP fluorescence intensity results mainly from expression of the reporter, and unstained cells expressing the reporter (blue) do not fall along a diagonal because autofluorescence contributes minimally. Similarly, autofluorescence contributes perhaps one-quarter of the total PE fluorescence in 3T3-L1 adipocytes or fibroblasts; in CHO cells this figure is reduced to 1–2%. As in 3T3-L1 cells, the distribution of each of the stained populations (basal and insulin-stimulated, shown in red and green, respectively) falls along a diagonal because the amount of myc epitope at the surface of each cell is proportional to the amount of the reporter present within that cell. Insulin stimulates the entire population to shift upward along the PE (myc) axis, with no change in the slope of the diagonal, consistent with exocytosis of the GLUT4 reporter equally and with no saturation of the recycling mechanism among the infected cells.

Figure 7:
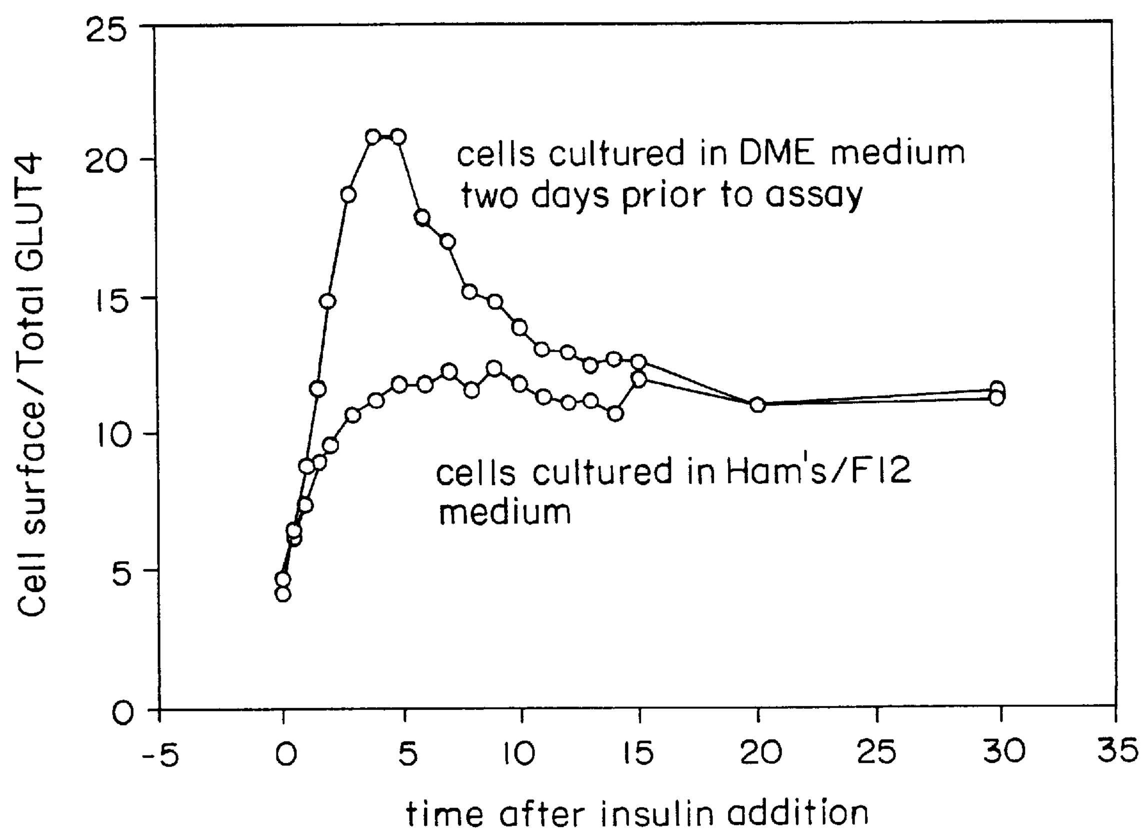
FIG. 7. Kinetics of GLUT4 externalization after insulin addition to CHO cells. CHO cells expressing the GLUT4 reporter are cultured in Han's/F12 medium (containing 10 mM glucose) until two days prior to the experiment, at which time some cells were placed in DME medium identical to that used for 3T3-L1 cells (containing 25 mM glucose). Cells were serum-starved for 3 hours, stimulated for various lengths of time with 80 nM insulin, chilled, stained for cell-surface myc epitope, and analyzed by FACS as described. CHO cells cultured in DME medium redistributed GLUT4 with biphasic kinetics, while those cultured in F12 externalized GLUT4 with an essentially monophasic response after insulin addition. These data suggest that GLUT4 is targeted to a highly insulin-responsive, intracellular compartment when CHO cells are cultured in DME medium, and that this compartment contains much less GLUT4 when the cells are cultured in F12 medium.

Changes in the proportion of GLUT4 at the cell surface of CHO cells stimulated for various amounts of time were assayed to determine if the kinetics of insulin-stimulated GLUT4 externalization are similar in CHO cells and in 3T3-L1 cells. To parallel the conditions used for 3T3-L1 cells, CHO cells were placed in DMEM two days before the experiment. As shown in FIG. 7, CHO cells respond to insulin with a dramatic redistribution of GLUT4 to the cell surface. As in 3T3-L1 cells, GLUT4 externalization peaks at four to five minutes after insulin addition, and then decreases to reach a steady-state by twenty minutes after insulin addition. The peak amount of GLUT4 at the cell surface is 5.5-fold more than the amount in unstimulated cells, and in several experiments 50% to 60% of this increase is eliminated in the subsequent decrease. Thus, while the final steady-state "fold-increase" in cell surface GLUT4 is less than in 3T3-L1 cells, this difference is minor and does not involve the initial response. Thus, GLUT4, when expressed in CHO cells, participates in an insulin-responsive recycling mechanism similar to that observed in 3T3-L1cells.

Discussion

The GLUT4 glucose transporter is expressed almost exclusively in adipose tissue and skeletal and cardiac muscle, where it accounts for the bulk of insulin-stimulated glucose uptake (Charron, et al., *J Biol Chem.* 274:3253–3256 (1999)). In these tissues, insulin stimulates the redistribution of GLUT4 from an intracellular site of sequestration to the plasma membrane (Cushman and Wardzala, *J Biol Chem.* 255:4758–4762 (1980); Suzuki and Kono, *Proc Natl Acad Sci USA.* 77:2542–2545 (1980); reviewed in Holman and Cushman, *Semin Cell Dev Biol.* 7:259–268 (1996); Pessin, et al., *J Biol Chem.* 274:2593–2596 (1999); Rea and James, *Diabetes.* 46:1667–1677 (1997). Another glucose transporter isoform, GLUT1, is also expressed in fat and muscle tissues and is present at high levels in many other cell types and in cultured cell lines. A large proportion of GLUT1 is present on the plasma membrane, even in the absence of insulin. Thus, while both GLUT1 and GLUT4 recycle at the plasma membrane, only GLUT4 recycling is characterized by significant intracellular sequestration—resulting from a slow rate of exocytosis—in the absence of insulin. Insulin increases the rate of GLUT4 exocytosis, with little or no decrease in its rate of endocytosis, so that in adipocytes the proportion of GLUT4 at the cell surface increases from ≦10% in the absence of insulin to approximately 50% in its presence (Jhun, et al., *J Biol Chem.* 267:17710–17715 (1992); Yang, J. and Holman, *J Biol Chem.* 268:4600–4603 (1993); Satoh, et al., *J Biol Chem.* 268:17820–17829 (1993); Yeh, et al., *Biochemistry* 34;15523–1553 1 (1995).

The intracellular compartment responsible for sequestering and for mobilizing GLUT4 after insulin addition has been presumed to be present only in adipose and muscle cells. Indeed, there have been attempts by several investigators to clone proteins involved in GLUT4 trafficking based on the premise that these are induced during adipogenesis (Baldini, et al. *Proc Natl Acad Sci USA.* 89:5049–5052 (1992). Most work has utilized either primary adipocytes or 3T3-L1 cells, which can be propagated as fibroblasts and induced to undergo adipocyte differentiation over the course of eight days (Green and Kehinde, *Cell.* 5:19–27 (1975); Rubin, et al., *J Biol Chem.* 253:7570–7578 (1978). GLUT4, like several other adipocyte-specific proteins, is induced at day 5. Previous work indicates that the mechanism for GLUT4 sequestration is present before GLUT4 itself is expressed at significant levels (Yang, et al., *Biol Chem.* 267:1039310399 (1992). Recent studies of endogenous GLUT1, transferrin receptor (TfnR)[1], and insulin-responsive aminopeptidase (IRAP) in 3T3-L1 cells suggest that the compartment responsible for basal GLUT4 sequestration is not present in undifferentiated 3T3-L1 fibroblasts but develops at day 3 (El-Jack, et al., *Mol Biol Cell.* 10: 1581–1594 (1999); Ross, et al., *Biochem J.* 330:1003–1008 (1998)). Thus, it has been argued that the development of a specialized, insulin-responsive compartment to which GLUT4 is targeted results from the expression of as yet unknown genes early during 3T3-L1 adipocyte differentiation.

Other investigations suggest that an insulin-responsive compartment, similar to that containing GLUT4 in adipocytes, may be present in a wide variety of cell types. Intracellular sequestration of exogenously expressed GLUT4, though usually without insulin responsiveness, has been observed in 3T3-L1 fibroblasts, HepG2 cells, Xenopus oocytes, COS cells, Chinese Hamster ovary (CHO) cells, NIH 3T3 cells, and PC12 cells (Asano, et al., *J Biol Chem.* 267:19636–19641 (1992); Czech, et al., *J Cell Biol.*

123:127–135 (1993); Haney, et al., *J Cell Biol.* 1 14:689–699 (1991); Herman, et al., *Proc Natl Acad Sci USA.* 91:12750–12754 (1994); Hudson, et al., *J Cell Biol.* 116:785–797 (1992); Marshall, et al., *J Biol Chem.* 268:26193–26199 (1993); Schurmann, et al., *Biochim Biophys Acta.* 1131:245–252 (1992); Shibasaki, et al., *Biochem J.* 281;829–834 (1992); Verhey, et al., *J Cell Biol.* 123:137–147 (1993). When expressed in PC 12 neuroendocrine cells, GLUT4 is targeted to a class of organelles distinct from both secretory granules and synaptic vesicles; a similar compartment is found in transfected NIH 3Y3 and CHO cells and in rat adipocytes (Herman, et al., *Proc Natl Acad Sci USA.* 91:12750–12754 (1994)). Transfected GLUT4 expressed in CHO cells is sequestered intracellularly because of a slow rate of recycling to the plasma membrane; exocytosis is stimulated by insulin and GLUT4 trafficking is clearly distinct from that of GLUT1 (Kanai, et al., *J Biol Chem.* 268:14523–14526 (1993); Ishii, K. et al., *Biochem J* 309:813–823 (1995); Araki, et al., *Biochem J.* 315:153–159 (1996); Dobson, et al., *FEBS Lett.* 393: 170–184 (1996)). Yet, these and other studies of GLUT4 trafficking are difficult to interpret because they employed experimental systems that may not be relevant to GLUT4 trafficking in fat and muscle. Indeed, the CHO cells used for many of these studies were stably transfected not only with GLUT4, but, with the insulin receptor as well (Kanai, et al., *J Biol Chem.* 268:14523–14526 (1993); Ishii, et al., *Biochem J.* 309:813–823 (1995)).

A major difficulty in studying GLUT4 trafficking has been the lack of a sensitive, specific, and quantitative assay to measure changes in the proportion of GLUT4 at the cell surface. Previous methods have included isolation of plasma membrane and low density microsomal fractions, bis-mannose photolabeling of cell surface GLUT4 followed by immunoprecipitation, and preparation of plasma membrane sheets followed by microscopy (Cushman and Wardzala., *J Biol Chem.* 255:4758–4762 (1980); Holman, et al., *J Biol Chem.* 265:18172–18179 (1990); Robinson, et al., *J Cell Biol.* 117:1181–1196 (1992); reviewed in Li and McNeill, *J Pharmacol Toxicol Methods.* 38:1–10 (1997). These assays are laborious and/or subject to interassay variability, and at best are semiquantitative. Glucose uptake is confounded by the presence of GLUT1 in the plasma membrane. Detection of an epitope tag placed in the first exofacial loop of exogenously expressed GLUT4 protein has the potential to be quantitative and specific, but in its original manifestation suffered from high background and resultant poor sensitivity (Kanai, et al., (1993)). Expression of a chimeric protein containing GLUT4 fused in-frame to green fluorescent protein (GFP) has allowed visualization of membrane trafficking by video fluorescence microscopy in individual CHO or 3T3-L1 cells, yet this technique does not allow quantitation of cell surface GLUT4 (Dobson, et al., *FEBS Lett.* 393:179–184 (1996); Oatey, et al., *Biochem J.* 327:637–642 (1997)).

Described herein is a novel assay for GLUT4 trafficking at the plasma membrane. A modified GLUT4 protein which contains seven myc epitope tags in the first exofacial loop as well as GFP fused in-frame at the carboxy terminus was expressed, using a retroviral vector. As described herein, results demonstrate that this protein is targeted appropriately in 3T3-L1adipocytes. Flow cytometry was used to measure, on a cell-by-cell basis, changes in the proportion of GLUT4 at the plasma membrane. This assay was also used to demonstrate that insulin stimulates GLUT4 exocytosis at all times during 3T3-L1 cell differentiation, even in undifferentiated, confluent fibroblasts. This effect of insulin is blocked by phosphatidylinositol 3'-kinase (PI3K) inhibitors and is kinetically indistinguishable at all stages of 3T3-L1 cell differentiation. In all cases, insulin removal results in reinternalization of the reporter, and readdition of insulin stimulates recycling to the cell surface. As also described herein, insulin has been shown to stimulate externalization of the GLUT4 reporter in CHO cells with biphasic kinetics identical to those in 3T3-L1cells. Thus, GLUT4 participates in an insulin-regulated endocytic recycling pathway that is present in undifferentiated 3T3-L1 fibroblasts and CHO cells, no 3T3-L1 adipocyte-specific proteins are required. Thus GLUT4 employs an insulin-regulated recycling mechanism that is likely present in many types of cells.

As described herein, Applicants have shown that insulin triggers rapid exocytosis of GLUT4 in several diverse cell types (3T3-L1 adipocytes, 3T3-L1 fibroblasts, and CHO cells). This conclusion is based on studies using a novel, FACS-based assay to measure changes in the proportion of GLUT4 present at the plasma membrane. This action of insulin is blocked by either of two structurally dissimilar PI3K inhibitors in 3T3-L1 cells at all stages of differentiation, suggesting that identical signaling mechanisms are involved. Moreover, insulin stimulates GLUT4 externalization with identical, biphasic kinetics at all times during 3T3-L1 differentiation, and reinternalization and recycling of the reporter protein has been demonstrated as well. Strikingly, insulin triggers externalization of the GLUT4 reporter protein in CHO cells, and the kinetics of this response are biphasic and identical to those observed in 3T3-L1 cells, when CHO cells are cultured under identical conditions to those used for 3T3-L1 cells.

The use of a GLUT4 reporter with both an exofacial epitope tag and GFP fused to the cytosolic tail is a significant advance over previous assays for GLUT4 trafficking at the cell surface because it allows accurate quantitation of changes in the proportion—rather than the amount—of GLUT4 that is present at the cell surface. These measurements are made on a cell-by-cell basis using flow cytometry, with the result that alterations in cell-surface GLUT4 targeting are determined with high specificity and precision. Importantly, Applicants have shown that this reporter protein is reinternalized after insulin removal, and that it recycles to the plasma membrane after restimulation with insulin. The time course for GLUT4 reinternalization is slightly prolonged in 3T3-L1 adipocytes as compared to fibroblasts; this may be because adipocytes express a greater number of insulin receptors, which are endocytosed with bound insulin (Reed and Lane, *Proc Natl Acad,Sci USA.* 77:285–289 (1980)). Thus, insulin removal may not effectively stop insulin signaling in adipocytes. Applicants isolated a stable population of cells that express a moderate amount of the reporter protein, so as to avoid saturation of the trafficking mechanism. The use of flow cytometry, as well as the presence of several, tandem epitope tags, made it possible to measure small amounts of cell-surface and total reporter. Finally, the present method allows rapid analysis of multiple samples, making possible the detailed kinetic studies presented here.

Multiple GLUT4 Traffickinq Compartments

Characterization of the intracellular, insulin-responsive GLUT4-containing compartment has been complicated by the fact that GLUT4 resides in several morphologically distinct locations within the cell. Ultrastructural studies have shown that GLUT4 is present in peripheral tubulovesicular structures distinct from lysosomes, as well as in a perinuclear compartment that is in close proximity to the trans-Golgi network (Slot, et al., *Proc Natl Acad Sci USA.*

88:7815–7819 (1991); Slot, et al., *J Cell Biol.* 113:123–135 (1991); Smith, et al., *Proc Natl Acad Sci USA.* 88:6893–6897 (1991); Hudson, et al., *J Cell Biol.* 116:785–797 (1992)). Recent work indicates that approximately 40–45% of intracellular GLUT4 distributes to a TfnR-positive endosomal compartment, while 50–60% is in a second, TfnR-negative compartment; it is this TfnR-negative compartment that is mobilized upon insulin addition (Livingstone, et al., *Biochem J.* 315:487–495 (1996); Aledo, et al., Biochem J. 325:727–732 (1997); Martin, et al., *Journal of Cell Science.* 110:2281–2291 (1997); Kandror and Pilch, *Biochem J.* 331:829–835 (1998)). Some data suggest that the TfnR-positive GLUT4 compartment is the precursor of the TfnR-negative, insulin responsive compartment (Wei, et al., *J. Cell Biol.* 140:565–575. (1998)). Moreover, targeting motifs within GLUT4 mediate its distribution between TfnR-negative and TFN-α-positive compartments (Melvin, et al., *Biochemistry.* 38:1456–1462 (1999)). It has previously been shown that 3T3-L1 adipocytes also possess an insulin-regulated secretory compartment containing ACRP30, a TNF-α like protein produced exclusively in adipocytes (Scherer, et al., *J Biol Chem.* 270:26746–26749 (1995); Shapiro and Scherer, *Curr Biol.* 8:335–338 (1998); Bogan and Lodish, *J Cell Biol.* 146: 609–620 (1999)). This regulated secretory compartment is distinct from the insulin-regulated GLUT4 compartment (Bogan and Lodish, *J Cell Biol.* 146: 609–620 (1999)). Previous work and the data presented here support the idea that proteins that are induced upon 3T3-L1 differentiation, such as Rab3D, may be involved in insulin-stimulated secretion but are not necessary for GLUT4 translocation.

Kinetic studies are broadly consistent with the notion that there are multiple compartments through which GLUT4 traffics. GLUT4 recycles between the plasma membrane and intracellular sites in both basal and insulin-stimulated states; the major effect of insulin is to increase the exocytosis rate constant with only a slight decrease the endocytosis rate constant (Jhun, et al., *J Biol Chem.* 267:17710–17715 (1992); Yang and Holman, *J Biol Chem.* 268:4600–4603 (1993); Satoh, et al., *J Biol Chem.* 268:17820–17829 (1993)). Yet, the initial insulin-stimulated externalization of GLUT4 is too rapid to be explained by the steady-state rate constants for exocytosis and endocytosis in the presence of insulin (Clark, et al., *Biochem J* 278:235–241 (1991); Yang and Holman, *J Biol Chem.* 268:4600–4603 (1993); Satoh, et al., *J Biol Chem.* 268:17820–17829 (1993)). It has therefore been argued that a 2-pool model, with one intracellular and one plasma membrane compartment, does not explain the observed kinetics of insulin-stimulated GLUT4 externalization, and that GLUT4 must traffic through three or more compartments. Among these compartments is postulated to be a highly insulin-responsive, intracellular compartment that is rapidly depleted of GLUT4 after acute insulin stimulation, such that the steady state exocytosis rate becomes limited at another step in the recycling pathway (Holman, et al., *J Biol Chem.* 269:17516–17524 (1994); Yeh, et al., *Biochemistry.* 34:15523–1553 1 (1995); Araki, et al., *Biochem J* 315:153–159 (1996)). This kinetically defined compartment presumably corresponds to the morphologically and biochemically defined, TfnR-negative compartment containing GLUT4.

The biphasic kinetics of GLUT4 externalization observed are consistent with these analyses, and cannot be explained by a model where first order kinetics govern the distribution of GLUT4 between two compartments. Thus, the initial, rapid externalization of GLUT4 represents mobilization of a highly insulin-responsive, intracellular GLUT4 pool. Subsequently, the proportion of GLUT4 at the cell surface decreases to a steady-state in the presence of insulin, determined by exocytosis and endocytosis rates involving other steps in the recycling pathway. The initial overshoot of the steady-state GLUT4 distribution after insulin stimulation was predicted by mathematical analysis, but measurement of GLUT4 in plasma membranes by subcellular fractionation or photolabeling did not convincingly demonstrate its occurrence (Clark, et al., *Biochem J.* 278:235–241 (1991); Satoh, et al., *J Biol Chem.* 268:17820–17829 (1993); Holman, et al., *J Biol Chem.* 269:17516–17524 (1994)). Observation of this phenomenon reflects the improved sensitivity of the assay, although this may also reflect differences between 3T3-L1 cells and primary rat adipocytes, which were used for previous kinetic studies. Finally, measurement of the initial rate of GLUT4 externalization is more rapid than reported by Clark, et al., *Biochem J.* 278:235–241 (1991), although the results presented herein are quite similar to those of Satoh, et al., *J Biol Chem.* 268:17820–17829 (1993). Careful examination of the latter group's data suggests a slight overshoot of the insulin-stimulated steady-state response in primary rat adipocytes, although at the time this appears to have been attributed to error in the measurement (see FIG. 6A of Satoh, et al., *J Biol Chem.* 268:17820–17829 (1993)).

Insulin-triggered GLUT4 Externalization in 3T3-L1 Fibroblasts and CHO Cells

Identical kinetics of GLUT4 externalization were observed after insulin stimulation of 3T3-L1 adipocytes, 3T3-L1 fibroblasts, and CHO cells, and in all instances insulin addition results in an initial overshoot of the steady-state GLUT4 distribution. Thus, all of these cell types contain a highly insulin-responsive recycling mechanism in which GLUT4 participates. Compared to the peak response, the steady-state proportion of GLUT4 on the plasma membrane in the presence of insulin is less in CHO cells than in 3T3-L1cells; presumably this reflects differences in the endocytosis and exocytosis rate constants for pools other than the highly insulin-responsive pool. These results for 3T3-L1cells are consistent with those of Yang, et al., *J Biol Chem.* 267:1039310399 (1992), who suggested that the mechanism for GLUT4 sequestration in 3T3-L1adipocytes is present before GLUT4 is expressed. The results presented herein clearly demonstrate that insulin-responsive GLUT4 trafficking does not require the expression of adipocyte-specific proteins that are upregulated during 3T3-L1 differentiation.

Other investigations have studied GLUT1, TfnR, and IRAP in attempts to determine when, during 3T3-L1 differentiation, the highly insulin-responsive GLUT4 recycling mechanism develops. Biochemical analyses of GLUT1 and TfnR indicate that intracellular sequestration of these proteins in the absence of insulin is enhanced on Day 3 of 3T3-L1 differentiation. Similar to this result, Applicants observe a greater sequestration of the GLUT4 reporter beginning on Day 2 of 3T3-L1 differentiation (FIGS. 3A and 4). This is a quantitative, rather than qualitative, difference and the mechanism for highly insulin-responsive GLUT4 exocytosis is nonetheless present in 3T3 -L1 fibroblasts. More importantly, GLUT1 and TfnR do not completely cotraffic with GLUT4, and therefore are of uncertain utility in studying the GLUT4 compartments.

Described herein is a highly insulin-responsive mechanism for GLUT4 externalization in CHO cells. It has previously been suggested that CHO cells are not a physiologically relevant cell type for the study of GLUT4 trafficking because they do not express endogenous GLUT4 and other adipocyte markers, and do not respond well to insulin (Shibasaki, et al., *Biochem J.* 281:829–834 (1992)). Others have argued that CHO cells may be a reasonable model for this process, since GLUT4 responds appropriately to insulin and pharmacologic agents (including PI3K inhibitors) in these cells (Kanai, et al., *J Biol Chem.* 268:14523–14526 (1993); Todaka, et al., *Biochem J* 315:875–882 (1996)). Yet, these studies of GLUT4 trafficking required overexpression of the insulin receptor, leading to further concerns about the physiologic relevancy of CHO cells. The data presented herein argue that CHO cells indeed contain an insulin-regulated recycling mechanism, similar to that in adipocytes, in which GLUT4 participates. The kinetics of GLUT4 externalization in CHO cells and 3T3-L1 cells are identical; in addition, the magnitude of the peak response is similar in CHO cells and in 3T3-L1 cells. A 5.5-fold increase in the proportion of GLUT4 at the surface of CHO cells were observed 5 minutes after insulin addition; by comparison, the average maximal increase in mature (Day 8 and 10) 3T3-L1 adipocytes is 5.4-fold (FIGS. 4 and 7). The CHO cells used in the work described herein were not transfected with the insulin receptor; thus, the endogenous level of insulin receptor expression in these cells is adequate to mediate this response. It is unclear why previous studies noted poorly insulin-responsive trafficking of GLUT4 in CHO cells not overexpressing the insulin receptor; possible explanations include differences in the assays used and/or the use of prolonged (≧15 min.) insulin stimulation.

Recent studies using a chimeric protein containing the cytoplasmic amino terminus of IRAP (insulin-response aminopeptidase) have identified an insulin-responsive, slow endocytic recycling mechanism in CHO cells (Johnson, et al., *J Biol Chem.* 273:17968–17977 (1998)). Conclusions presented herein are broadly in agreement with those reached by these investigators. Yet, Johnson and coworkers avoided the assertion that IRAP and GLUT4 share a trafficking pathway in CHO cells because 1) GLUT4 expressed in CHO cells was not thought to be translocated to the cell surface by insulin, and 2) IRAP appeared to reside in a TfnR (transferrin receptor)-positive compartment distinct from that to which GLUT4 is targeted. Data presented herein indicate that the first point is incorrect: GLUT4 does indeed translocate to the surface of CHO cells after insulin stimulation. The data presented herein do not address the second point. Nonetheless, it is reasonable to conclude that the GLUT4 reporter is utilizing the same recycling mechanism detected by Johnson and coworkers using an IRAP chimera. If GLUT4 and IRAP do indeed compete for tethering or sorting proteins, then the data presented herein suggest that these proteins are not specific to adipose and muscle tissues, but are more widely expressed.

More generally, the results presented are in agreement with biochemical observations that exogenously expressed GLUT4 is targeted to a distinct class of intracellular vesicles that may be present in many cell types, including PC 12 cells, CHO cells, and insulinoma cells (Herman, et al., *Proc Natl Acad Sci USA.* 91:12750–12754 1994); Thorens and Rot,. *J Cell Sci.* 109:1311–1323 (1996); Wei, et al., *J Cell Biol.* 140:565–575 (1998)). Other hormone-regulated exocytic processes may utilize a mechanism similar to that employed by GLUT4. For example, the activities of both the AQP2 water channel in the renal collecting duct and the $H^+/K^+$ ATPase in gastric parietal cells are regulated by recycling at the plasma membrane (Caplan, Curr Opin *Cell Biol.* 10:468–473 (1998); Knepper and Inoue, *Curr Opin Cell Biol.* 9:560–564 (1997); Brown, et al., *Am J Physiol.* 275:F328–331 (1998)). Recent data suggest that some of the same SNARE proteins involved in GLUT4 trafficking also play a role in AQP2 trafficking (Inoue, et al., *Am J Physiol.* 275:F752–760 (1998); Mandon, et al., *J Clin Invest.* 98:906–913 (1996); Nielsen, et al., *J Clin Invest.* 96:1834–1844 (1995); Rea and James, *Diabetes.* 46:1667–1677 (1997)). The degree to which these diverse proteins employ similar trafficking mechanisms is not known, and will require further study. Nonetheless, it seems likely that a recycling mechanism similar to that used by GLUT4 in adipose and muscle tissues is present in other hormone-responsive cells.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. Eukaryotic cells expressing modified protein of interest, wherein the protein of interest undergoes translocation in the eukaryotic cells upon contact with or exposure to a condition and wherein the modified protein of interest comprises the protein of interest and at least one detectable tag in an extracellular domain and at least one detectable tag in an intracellular domain thereof, wherein the at least one detectable tag in the intracellular domain is different from the at least one detectable tag in the extracellular domain.

2. Eukaryotic cells of claim 1, wherein the protein of interest is selected from the group consisting of: GLUT4; Aquaporin-2; Cystic Fibrosis Transmembrane conductance Regulator and gastric H+/K+ ATPase; the at least one detectable tag in the extracellular domain is an epitope tag and the at least one detectable tag in the intracellular domain is a fluorescent tag; and the cells are mammalian cells.

3. Mammalian cells of claim 2, wherein the modified protein of interest is expressed in the cells by a replication-deficient retrovirus encoding the modified protein of interest.

4. Mammalian cells of claim 2 that stably express modified protein of interest.

5. Mammalian cells of claim 2, wherein the at least one epitope tag is a myc epitope tag and the fluorescent tag in the intracellular domain is green fluorescent protein, blue fluorescent protein or red fluorescent protein.

6. Mammalian cells expressing modified protein of interest, wherein the modified protein of interest comprises at least one detectable tag in an extracellular domain and at least one detectable tag in an intracellular domain thereof, wherein the at least one detectable tag in the intracellular domain is a different from the at least one detectable tag in the extracellular domain.

7. Mammalian cells of claim 6, wherein the modified protein of interest is expressed in the cells by a replication-deficient retrovirus encoding the modified protein of interest.

8. Mammalian cells of claim 6 that stably express modified GLUT4 protein.

9. Mammalian cells of claim 7, wherein the at least one epitope tag is a myc epitope tag and the fluorescent tag in the intracellular domain is green fluorescent protein, blue fluorescent protein or red fluorescent protein.

10. Mammalian cells of claim 6 selected from the group consisting of: adipocytes, fibroblasts and muscle cells.

11. Mammalian cells of claim 10, wherein the cells are selected from the group consisting of: 3T3 L1 cells; Chinese Hamster Ovary cells; C2C12 cells and L6 cells.

12. Mammalian cells of claim 11, wherein the 3T3 L1 cells are undifferentiated.

13. Eukaryotic cells expressing modified GLUT4 protein, wherein the modified GLUT4 protein is GLUT4 protein comprising at least one detectable tag in an extracellular domain and at least one detectable tag in an intracellular domain thereof, wherein the at least one detectable tag in the intracellular domain is different from the at least one detectable tag in the extracellular domain.

14. Eukaryotic cells of claim 13, wherein the detectable tag in the extracellular domain is at least one epitope and the detectable tag in the intracellular domain is at least one fluorescent tag.

15. Mammalian cells of claim 14, wherein the modified GLUT4 protein is expressed in the cells by a replication-deficient retrovirus encoding the modified GLUT4 protein.

16. Mammalian cells of claim 14 that stably express modified GLUT4 protein.

17. Mammalian cells of claim 14, wherein the at least one epitope tag is a myc epitope tag and the fluorescent tag in the intracellular domain is green fluorescent protein, blue fluorescent protein or red fluorescent protein.

18. Mammalian cells of claim 14, wherein the modified GLUT4 protein comprises seven myc epitope tags and the fluorescent tag in the intracellular domain is green fluorescent protein, blue fluorescent protein or red fluorescent protein.

19. Mammalian cells expressing modified GLUT4 protein, wherein the modified GLUT4 protein is GLUT4 protein comprising at least one detectable tag in an extracellular domain and at least one detectable tag in an intracellular domain thereof, wherein the at least one detectable tag in the intracellular domain is different from the at least one detectable tag in the extracellular domain.

20. Mammalian cells of claim 19, wherein the modified GLUT4 protein is expressed in the cells by a replication-deficient retrovirus encoding the modified GLUT4 protein.

21. Mammalian cells of claim 20 that stably express modified GLUT4 protein.

22. Mammalian cells of claim 20, wherein the at least one epitope tag is a myc epitope tag and the fluorescent tag in the intracellular domain is green fluorescent protein, blue fluorescent protein or red fluorescent protein.

23. Mammalian cells of claim 22, wherein the modified GLUT4 protein comprises seven myc epitope tags.

24. Mammalian cells of claim 19 selected from the group consisting of: adipocytes, fibroblasts and muscle cells.

25. Mammalian cells of claim 24, wherein the cells are selected from the group consisting of: 3T3-L1 cells, Chinese Hamster Ovary cells, C2C12 cells and L6 cells.

26. Mammalian cells of claim 25, wherein the 3T3 L1 cells are undifferentiated.

27. Mammalian cells of claim 25, wherein the 3T3 L1 cells are differentiated.

28. Mammalian cells of claim 20 wherein the replication-deficient retrovirus is pMX-GLUT4myc7-GFP.

* * * * *